(12) United States Patent
Lin et al.

(10) Patent No.: US 8,586,707 B2
(45) Date of Patent: Nov. 19, 2013

(54) STAPLED PEPTIDES AND METHOD OF SYNTHESIS

(75) Inventors: Qing Lin, Getzville, NY (US); Mike Madden, N. Tonawanda, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 485 days.

(21) Appl. No.: 12/561,107

(22) Filed: Sep. 16, 2009

(65) Prior Publication Data

US 2010/0093086 A1 Apr. 15, 2010

Related U.S. Application Data

(60) Provisional application No. 61/097,357, filed on Sep. 16, 2008.

(51) Int. Cl.
*A61K 38/00* (2006.01)
*A61K 38/04* (2006.01)
*C07K 5/00* (2006.01)
*C07K 7/00* (2006.01)
*C07K 16/00* (2006.01)
*C07K 17/00* (2006.01)

(52) U.S. Cl.
USPC ........... 530/333; 530/329; 530/327; 530/300; 514/1.1

(58) Field of Classification Search
None
See application file for complete search history.

(56) References Cited

U.S. PATENT DOCUMENTS

| | | | |
|---|---|---|---|
| 6,783,763 B1* | 8/2004 | Choppin et al. | 424/204.1 |
| 2005/0250680 A1* | 11/2005 | Walensky et al. | 514/9 |
| 2006/0008848 A1 | 1/2006 | Verdine et al. | |
| 2007/0248567 A1* | 10/2007 | Pathak et al. | 424/78.27 |
| 2009/0088553 A1 | 4/2009 | Nash | |
| 2010/0093086 A1* | 4/2010 | Lin et al. | 435/375 |

FOREIGN PATENT DOCUMENTS

| | | |
|---|---|---|
| WO | 2008/076904 A1 | 6/2008 |
| WO | 2008/104000 A2 | 8/2008 |

OTHER PUBLICATIONS

Iwakura et al. Polymerizations by 1,3-dipolar cycloaddition reactions. IV. N,N'-Diphenylterephthalonitrilimine. Macromol. Chem. (1966), 97, 278-81 (abstract).*
PubChem CID 402857 (Pubchem Online) 2005 [Retrieved Jan. 21, 2010]; Retrieved from the internet URL<http://pubchem.ncb .n. m.n. h.gov/summary/summary.cg ?c d=402857& oc=ec_rcs>; 3 pages.*
Song et al. A photoinducible 1,3-dipolar cycloaddition reaction for rapid, selective modification of tetrazole-containing proteins. Angewandte Chemie, International Edition (2008), 47(15), 2832-2835 (Applicant's NPL publication).*
Madden et al. Facile synthesis of stapled, structurally reinforced peptide helices via a photoinduced intramolecular 1,3-dipolar cycloaddition reaction. Chemical Communications (Cambridge, United Kingdom) (2009), (37), 5588-5590.*
Song et al. A photoinducible 1,3-dipolar cycloaddition reaction for rapid, selective modification of tetrazole-containing proteins. Angewandte Chemie, International Edition (2008), 47(15), 2832-2835.*
Iwakura et al. Polymerizations by 1,3-dipolar cycloaddition reactions. IV. N,N'-Diphenylterephthalonitrilimine. Macromol. Chem. (1966), 97,278-81 (abstract).*
Voitekhovich et al.; Thermal Recyclization of 5-R-2-1sopropenyltetrazoles Into 5-R-3-Methylpyrazoles; Chemistry oi Heterocyc c Compounds, 2002, Vo. 38, No. 11 ; p. 1422.*
Song et al. A photoinducible 1,3-dipolar cycloaddition reaction for rapid, selective modification of tetrazole-containing proteins Angewandte Chemie, International Edition (2008), 47(15), 2832-2835.*
Bernal et al.; Reactivation of the p53 Tumor Suppressor Pathway by a Stapled p53 Peptide; J. Am. Chem. Soc., 2007, vol. 129; pp. 2456-2457 (DS of Aug. 18, 2010).*
Bernal et al.; Reactivation of the p53 Tumor Suppressor Pathway by a Stapled p53 Peptide; J. Am. Chem. Soc., 2007, vol. 129; pp. 2456-2457.
Voitekhovich et al.; Thermal Recyclization of 5-R-2-Isopropenyltetrazoles Into 5-R-3-Methylpyrazoles; Chemistry of Heterocyclic Compounds, 2002, vol. 38, No. 11; p. 1422.
PubChem CID 402857 (Pubchem Online) 2005 [Retrieved Jan. 21, 2010]; Retrieved from the internet URL:<http://pubchem.ncbi.nlm. nih.gov/summary/summary.cgi?cid=402857&loc=ec_rcs>; 3 pages.
Song, W. et al., Selective Functionalization of a Genetically Encoded Alkene-Containing Protein via "Photoclick Chemistry" in Bacterial Cells, Jul. 1, 2008, J. Am. Chem. Soc., vol. 130, No. 30, pp. 9654-9655.
Wang, Y., et al., Discovery of Long-Wavelength Photoactivatable Diaryltetrazoles for Bioorthogonal 1,3-Dipolar Cycloaddition Reactions, Aug. 1, 2008, Organic Letters, vol. 10, No. 17, pp. 3725-3728.
Wang, Y. et al., Fast Alkene Functionalization in Vivo by Photoclick Chemistry: HOMO Lifting of Nitrile Imine Dipoles, Jun. 18, 2009, Angew. Chem. Int. Ed., vol. 48, No. 29, pp. 5330-5333.

* cited by examiner

*Primary Examiner* — Maury Audet
(74) *Attorney, Agent, or Firm* — Hodgson Russ LLP

(57) ABSTRACT

A method for preparing stapled peptides. The stapled peptides, including helical stapled peptides, are prepared according to a photochemically-based method, a [3+2] cycloaddition reaction. The helical stapled peptides exhibit increased helicity, thermal stability and cell permeability.

5 Claims, 12 Drawing Sheets

Stapling Reaction

Linear Peptide

Stapled Peptide

Table 1 Synthesis of stapled peptides based on the Karle and Balaram's heptapeptidic $3_{10}$ helix[a]

| Linear peptide | n | X | $R^1$ | $R^2$ | product | Yield (%) |
|---|---|---|---|---|---|---|
| 1 | 3 | - | Me | H | 9 | 15 |
| 2 | 3 | -Ph- | Me | H | 10 | 15 |
| 3 | 4 | - | Me | H | 11 | 41 |
| 4 | 4 | -Ph- | Me | H | 12 | 38 |
| 5 | 4 | - | H | OMe | 13 | 61 |
| 6 | 4 | - | Me | OMe | 14 | 53 |
| 7 | 4 | - | H | $NMe_2$ | 15 | 63 |
| 8 | 4 | - | Me | $NMe_2$ | 16 | 94 |

[a]The reaction was performed by irradiating linear peptides (150 μM in acetonitrile) in a quartz round-bottom flask with a handheld UV lamp at 302 nm.

17: Ac-Val-Lys(Ac)-Leu-Aib-Val-Lys(Ac)-Leu-NH$_2$
(SEQ ID NO:1)

(SEQ ID NO:4)

(SEQ ID NO:4)

| linear peptide | solvent | product | yield (%) |
| --- | --- | --- | --- |
| 8 | MeCN | 16 | 87 |
| 8 | DCM | 16 | 43 |
| 8 | EtOAc | 16 | 86 |
| 8 | EtOH | 16 | 92 |
| 8 | $^i$PrOH | 16 | 88 |
| 8 | EtOH/H$_2$O (1:1) | 16 | 88 |

SEQUENCE LISTING

```
<160> NUMBER OF SEQ ID NOS: 13

<210> SEQ ID NO 1
<211> LENGTH: 7
<212> TYPE: PRT
<213> ORGANISM: artificial sequence
<220> FEATURE:
<223> OTHER INFORMATION: Artificial sequence with unknown amino acids
      due to possible amino acid modifications at the indicated
      positions yielding completely syntehsized peptide; Xaa at position
      4 is Aib
<220> FEATURE:
<221> NAME/KEY: misc_feature
<222> LOCATION: (2)..(2)
<223> OTHER INFORMATION: Xaa can be any naturally occurring or modified
      amino acid
<220> FEATURE:
<221> NAME/KEY: misc_feature
<222> LOCATION: (4)..(4)
<223> OTHER INFORMATION: Xaa is Aib
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1

Val Xaa Leu Xaa Val Xaa Leu
1               5

<210> SEQ ID NO 2
<211> LENGTH: 12
<212> TYPE: PRT
<213> ORGANISM: human

<400> SEQUENCE: 2

Glu Thr Phe Ser Asp Leu Trp Lys Leu Leu Pro Glu
```

-continued

```
1               5                   10

<210> SEQ ID NO 3
<211> LENGTH: 12
<212> TYPE: PRT
<213> ORGANISM: artificial sequence
<220> FEATURE:
<223> OTHER INFORMATION: synthesized peptide

<400> SEQUENCE: 3

Leu Thr Phe Glu His Tyr Trp Ala Gln Leu Thr Ser
1               5                   10

<210> SEQ ID NO 4
<211> LENGTH: 12
<212> TYPE: PRT
<213> ORGANISM: artificial sequence
<220> FEATURE:
<223> OTHER INFORMATION: artificial peptide sequence with unknown amino
      acids due to modifications of amino acids at the indicated
      positions yielding completely syntehsized sequence
<220> FEATURE:
<221> NAME/KEY: misc_feature
<222> LOCATION: (4)..(4)
<223> OTHER INFORMATION: Xaa can be any naturally occurring or modified
      amino acid
<220> FEATURE:
<221> NAME/KEY: misc_feature
<222> LOCATION: (11)..(11)
<223> OTHER INFORMATION: Xaa can be any naturally occurring or modified
      amino acid

<400> SEQUENCE: 4

Leu Thr Phe Xaa His Tyr Trp Ala Gln Leu Xaa Ser
1               5                   10

<210> SEQ ID NO 5
<211> LENGTH: 12
<212> TYPE: PRT
<213> ORGANISM: Artificial sequence
<220> FEATURE:
<223> OTHER INFORMATION: artificial peptide sequence with unknown amino
      acids due to modifications of amino acids at the indicated
      positions yielding completely syntehsized sequence
<220> FEATURE:
<221> NAME/KEY: misc_feature
<222> LOCATION: (4)..(4)
<223> OTHER INFORMATION: Xaa can be any naturally occurring or modified
      amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 5

Leu Thr Phe Xaa His Tyr Trp Xaa Gln Leu Thr Ser
1               5                   10

<210> SEQ ID NO 6
<211> LENGTH: 12
<212> TYPE: PRT
<213> ORGANISM: artificial sequence
<220> FEATURE:
<223> OTHER INFORMATION: artificial peptide sequence with unknown amino
      acids due to modifications of amino acids at the indicated
      positions yielding completely syntehsized sequence
<220> FEATURE:
<221> NAME/KEY: misc_feature
<222> LOCATION: (5)..(5)
<223> OTHER INFORMATION: Xaa can be any naturally occurring or modified
      amino acid
<220> FEATURE:
<221> NAME/KEY: misc_feature
```

```
<222> LOCATION: (9)..(9)
<223> OTHER INFORMATION: Xaa can be any naturally occurring or modified
      amino acid

<400> SEQUENCE: 6

Leu Thr Phe Glu Xaa Tyr Trp Ala Xaa Leu Thr Ser
1               5                   10

<210> SEQ ID NO 7
<211> LENGTH: 12
<212> TYPE: PRT
<213> ORGANISM: Artificial sequence
<220> FEATURE:
<223> OTHER INFORMATION: artificial peptide sequence with unknown amino
      acids due to modifications of amino acids at the indicated
      positions yielding completely syntehsized sequence
<220> FEATURE:
<221> NAME/KEY: misc_feature
<222> LOCATION: (4)..(4)
<223> OTHER INFORMATION: Xaa can be any naturally occurring or modified
      amino acid
<220> FEATURE:
<221> NAME/KEY: misc_feature
<222> LOCATION: (8)..(8)
<223> OTHER INFORMATION: Xaa can be any naturally occurring or modified
      amino acid

<400> SEQUENCE: 7

Leu Thr Phe Xaa His Tyr Trp Xaa Arg Leu Thr Ser
1               5                   10

<210> SEQ ID NO 8
<211> LENGTH: 12
<212> TYPE: PRT
<213> ORGANISM: artificial sequence
<220> FEATURE:
<223> OTHER INFORMATION: artificial peptide sequence with unknown amino
      acids due to modifications of amino acids at the indicated
      positions yielding completely syntehsized sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring or modified
      amino acid

<400> SEQUENCE: 8

Leu Thr Phe Xaa His Tyr Trp Xaa Arg Leu Arg Ser
1               5                   10

<210> SEQ ID NO 9
<211> LENGTH: 12
<212> TYPE: PRT
<213> ORGANISM: artificial sequence
<220> FEATURE:
<223> OTHER INFORMATION: artificial peptide sequence with unknown amino
      acids due to modifications of amino acids at the indicated
      positions yielding completely syntehsized sequence
<220> FEATURE:
<221> NAME/KEY: misc_feature
<222> LOCATION: (4)..(4)
<223> OTHER INFORMATION: Xaa can be any naturally occurring or modified
      amino acid
<220> FEATURE:
<221> NAME/KEY: misc_feature
<222> LOCATION: (8)..(8)
<223> OTHER INFORMATION: Xaa can be any naturally occurring or modified
      amino acid

<400> SEQUENCE: 9
```

Thr Ser Phe Xaa Gln Tyr Trp Xaa Leu Leu Ser Pro
1               5                   10

<210> SEQ ID NO 10
<211> LENGTH: 12
<212> TYPE: PRT
<213> ORGANISM: artificial sequence
<220> FEATURE:
<223> OTHER INFORMATION: artificial peptide sequence with unknown amino
      acids due to modifications of amino acids at the indicated
      positions yielding completely syntehsized sequence
<220> FEATURE:
<221> NAME/KEY: misc_feature
<222> LOCATION: (5)..(5)
<223> OTHER INFORMATION: Xaa can be any naturally occurring or modified
      amino acid
<220> FEATURE:
<221> NAME/KEY: misc_feature
<222> LOCATION: (9)..(9)
<223> OTHER INFORMATION: Xaa can be any naturally occurring or modified
      amino acid

<400> SEQUENCE: 10

Thr Ser Phe Ala Xaa Tyr Trp Asn Xaa Leu Ser Pro
1               5                   10

<210> SEQ ID NO 11
<211> LENGTH: 12
<212> TYPE: PRT
<213> ORGANISM: artificial sequence
<220> FEATURE:
<223> OTHER INFORMATION: artificial peptide sequence with unknown amino
      acids due to modifications of amino acids at the indicated
      positions yielding completely syntehsized sequence
<220> FEATURE:
<221> NAME/KEY: misc_feature
<222> LOCATION: (4)..(4)
<223> OTHER INFORMATION: Xaa can be any naturally occurring or modified
      amino acid
<220> FEATURE:
<221> NAME/KEY: misc_feature
<222> LOCATION: (11)..(11)
<223> OTHER INFORMATION: Xaa can be any naturally occurring or modified
      amino acid

<400> SEQUENCE: 11

Thr Ser Phe Xaa Gln Tyr Trp Asn Leu Leu Xaa Pro
1               5                   10

<210> SEQ ID NO 12
<211> LENGTH: 12
<212> TYPE: PRT
<213> ORGANISM: artificial sequence
<220> FEATURE:
<223> OTHER INFORMATION: artificial peptide sequence with unknown amino
      acids due to modifications of amino acids at the indicated
      positions yielding completely syntehsized sequence
<220> FEATURE:
<221> NAME/KEY: misc_feature
<222> LOCATION: (4)..(4)
<223> OTHER INFORMATION: Xaa can be any naturally occurring or modified
      amino acid
<220> FEATURE:
<221> NAME/KEY: misc_feature
<222> LOCATION: (8)..(8)
<223> OTHER INFORMATION: Xaa can be any naturally occurring or modified
      amino acid

<400> SEQUENCE: 12

Thr Ser Phe Xaa Arg Tyr Trp Xaa Arg Leu Ser Pro
1               5                   10

<210> SEQ ID NO 13

```
-continued

<211> LENGTH: 12
<212> TYPE: PRT
<213> ORGANISM: artificial sequence
<220> FEATURE:
<223> OTHER INFORMATION: artificial peptide sequence with unknown amino
      acids due to modifications of amino acids at the indicated
      positions yielding completely syntehsized sequence
<220> FEATURE:
<221> NAME/KEY: misc_feature
<222> LOCATION: (4)..(4)
<223> OTHER INFORMATION: Xaa can be any naturally occurring or modified
      amino acid
<220> FEATURE:
<221> NAME/KEY: misc_feature
<222> LOCATION: (8)..(8)
<223> OTHER INFORMATION: Xaa can be any naturally occurring or modified
      amino acid

<400> SEQUENCE: 13

Thr Ser Phe Xaa Gln Tyr Trp Xaa Arg Leu Arg Pro
1               5                   10
```

STAPLED PEPTIDES AND METHOD OF SYNTHESIS

CROSS-REFERENCE TO RELATED APPLICATIONS

This application claims priority to U.S. Provisional Patent Application No. 61/097,357, filed Sep. 16, 2008, the disclosure of which is incorporated herein by reference.

FIELD OF THE INVENTION

The present invention is related to functionalized peptides, and more particularly, the present invention is related to stapled peptides.

BACKGROUND OF THE INVENTION

Peptide helices are frequent mediators of key protein-protein interactions that regulate important biological processes. However, when peptide helices are taken out of protein context and placed into aqueous solution, they usually adopt random-coil conformations, leading to drastic reduction in biological activity and thus diminished therapeutic potential. Side chain crosslinking ("peptide stapling") is one of the numerous strategies that aim to stabilize and/or mimic peptide helices. Because peptide stapling necessitates macrocyclization, an entropically unfavorable process, very few reactions are known to date that give rise to reasonable yields without undesirable side reactions. Such reactions include intramolecular disulfide bond formation, lactam formation and ruthenium-catalyzed ring-closing metathesis (RCM).

Since protein-embedded peptide α-helices are key structural elements that regulate signaling pathways in cancer, HIV, and other diseases, stapled peptide α-helices have potential in therapeutic applications. Based on the foregoing, there is an ongoing, unmet need for the development of stapled peptides.

BRIEF SUMMARY OF THE INVENTION

The present invention provides an intramolecular, nitrile imine-mediated cycloaddition reaction ("photoclick chemistry") based method for the synthesis of stapled peptides. The invention also provides stapled peptides produced by this reaction. The photoclick chemistry-based stapling strategy provides a straightforward procedure and reasonable reaction yields. This unique peptide stapling chemistry can be particularly useful for the preparation of fluorescent peptide probes and bioactive peptide therapeutics.

The method of the present invention for preparing stapled peptides (e.g., helical peptides) includes the steps of: (a) providing a functionalized peptide comprising at least two amino acids, a first amino acid functionalized with an alkene moiety and a second amino acid functionalized with a tetrazole moiety, the two amino acids being in such proximity that the alkene and tetrazole moieties can react for form a pyrazoline moiety; (b) exposing the functionalized peptide to electromagnetic radiation of a suitable wavelength, such that the alkene moiety and the tetrazole moiety react to form a pyrazoline cross-linking moiety, thereby forming a stapled peptide. The method is graphically depicted in FIG. 1.

In one embodiment, a peptide of the invention has the amino acid sequence generally represented by the sequence Val Xaa Leu Gly Val Xaa Leu (SEQ ID NO:1), wherein the Xaa amino acids are a functionalized amino acid. Examples of such peptides are described in Example 2.

Without intending to be bound by any particular theory, it is considered that on exposure to a suitable wavelength of electromagnetic radiation the tetrazole moiety undergoes a cycloreversion reaction to generate a nitrile imine dipole which reacts with a proximate alkene dipolarophile in a 1,3- or [3+2] cycloaddition reaction resulting in formation of a pyrazoline moiety.

The term "staple" as used herein refers to the intramolecular or intermolecular connection (also referred to as cross-linking) of two peptides or two peptide domains (e.g., two loops of a helical peptide). When the peptide has a helical secondary structure, the staple is a macrocyclic ring, which is exogenous (not part of) core or inherent (non-stapled) helical peptide structure. The macrocyclic ring is comprised of a pyrazoline ring and incorporates at least two amino acids of the peptide. The size of the macrocyclic ring is determined by the number of helical peptide amino acids (y) in the ring and the number methylene groups in the moieties connecting the pyrazoline group to the peptide (m and n). The stapled peptide has a least one peptide. In various embodiments, the stapled peptide has 1, 2, or 3 staples.

The stapled peptide has at least one staple which comprises a pyrazoline moiety, which is a five-member, di-nitrogen heterocyclic ring. For example, the pyrazoline moiety can be represented by the following structure:

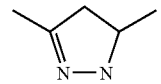

When the stapled peptide is a helical peptide, the pyrazoline ring is part of the exogenous macrocyclic ring which connects two loops of the α-helical peptide structure. For example, see the stapled peptide in FIG. 2. Typically, the face of each successive loop is stapled by incorporating amino acids i to i+3, i+4, i+7, i+11, etc. in the macrocyclic ring.

Illustrative functionalized peptides are shown in Example 1, FIG. 3 and FIG. 8(a). Illustrations of stapled peptides are shown in Examples 1 and 2, FIG. 3 and FIG. 8(a).

In some embodiments, the stapled peptides of the present invention exhibit increased α-helical stability in aqueous solution compared to a corresponding non-stapled peptide. In other embodiments, the stapled peptide exhibits increased thermal stability compared to a corresponding non-stapled peptide. In yet other embodiments, the stapled peptide exhibits increased biological activity compared to a corresponding non-stapled polypeptide. In still other embodiments, the stapled peptide exhibits increased resistance to proteolytic degradation compared to a corresponding non-stapled peptide. In yet other embodiments, the stapled peptide exhibits increased ability to penetrate living cells compared to a corresponding non-stapled peptide.

In one aspect, the present invention provides a method for transporting a helical peptide into a cell. In one embodiment, the method comprises the steps of: (a) providing a stapled peptide, and (b) contacting a cell with a composition comprising the stapled peptide, wherein a detectible fraction of the stapled peptide is transported into the cell. The detectible fraction of stapled peptide transported in a cell can be detected, for example, by optical fluorescence spectroscopy.

In another aspect, the present invention provides stapled peptides for treatment of an individual for a diseased state. The diseased state is one which can be affected by treatment with a composition comprising one or more stapled peptides of the present invention. An example of a diseased state is one which is affected by interaction of a stapled peptide with a cell, such that a gene or protein is up-regulated or down-regulated. In one embodiment, a therapeutic amount of a composition comprising a stapled peptide is administered to an individual to affect a diseased state.

DESCRIPTION OF INVENTION

The present invention provides an intramolecular, nitrile imine-mediated cycloaddition reaction ("photoclick chemistry") based method for the synthesis of stapled peptides. The invention also provides stapled peptides produced by this reaction. The photoclick chemistry-based stapling strategy provides a straightforward procedure and reasonable reaction yields. Additionally, stapled peptides exhibit distinct fluorescence with the emission wavelength serving as an indicator of the macrocyclic ring strain. This unique peptide stapling chemistry can be particularly useful for the preparation of fluorescent peptide probes and bioactive peptide therapeutics.

Figure 1:
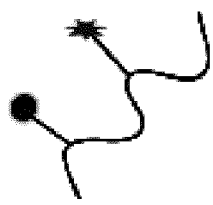
FIG. 1. Graphical depiction of peptide stapling reaction.
Figure 1:
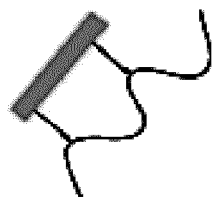

The method of the present invention for preparing stapled peptides includes the steps of: (a) providing a functionalized peptide comprising at least two amino acids, a first amino acid functionalized with an alkene moiety and a second amino acid functionalized with a tetrazole moiety, the two amino acids being in such proximity that the alkene and tetrazole moieties can react for form a pyrazoline moiety; (b) exposing the functionalized peptide to electromagnetic radiation of a suitable wavelength and length of time, such that the alkene moiety and the tetrazole moiety react to form a pyrazoline cross-linking moiety, thereby forming a stapled peptide. The method is graphically depicted in FIG. 1.

In one embodiment, the method of the present invention consists essentially of the steps provided above. In another embodiment, the method of the present invention consists of the steps provided above. In one embodiment, the present invention includes stapled peptides prepared according to the above-described method.

In one embodiment, the functionalized peptide has the following formula (Structure I):

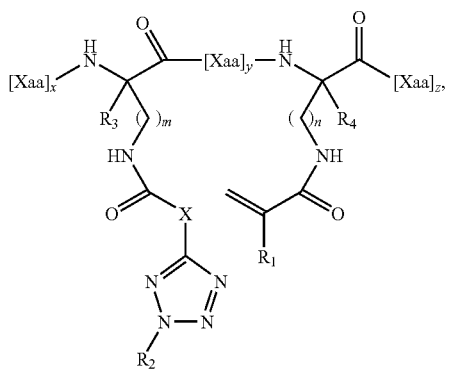

where the secondary structure of the peptide is α-helical. $R_1$ is H or an alkyl group with 1 to 6 carbons. $R_2$ is a phenyl group, a substituted phenyl group (such as alkoxy-, dialkylamino-substituted phenyl groups, and the like), or a heterocyclic group. $R_3$ is H or an alkyl group with 1 to 6 carbons. $R_4$ is H or alkyl group with 1 to 6 carbons. X is a phenyl group, substituted phenyl group, heterocyclic group, or a direct linkage between the carbonyl and tetrazole moieties. The number of carbons (e.g., methylene groups) comprising a tether between the α-carbon of the functionalized amino acid and either, the tetrazole moiety or alkene moiety, m or n, respectively, is independently 1 to 6. [Xaa] is any natural or synthetic amino acid. The number of amino acids in the peptide (in addition to the functionalized amino acids) is represented by x, y, and z, each of which can be from 1 to 10. The R groups (including the alkyl groups in any of the foregoing R groups, which can be linear or branched) can be substituted with functional groups such as halogens (including fluorine, chlorine, bromine, and iodine), alcohols, amines, ethers, esters, thiols, thioethers, thioesters, amides, and the like. Exposure of the peptide of Structure I to electromagnetic radiation of a suitable wavelength, such that the alkene moiety and tetrazole moiety react to form a pyrazoline moiety, results in formation of a peptide of Structure II (shown below).

The peptide can include both naturally-occurring and synthetic amino acids. The term "alpha(α)-amino acid" or simply "amino acid" refers to a molecule containing both an amino group and a carboxyl group bound to a carbon which is designated the α-carbon. Suitable amino acids include, without limitation, both the D- and L-isomers of the naturally-occurring amino acids, as well as non-naturally occurring amino acids prepared by organic synthesis or other metabolic routes. Unless the context specifically indicates otherwise, the term amino acid, as used herein, is intended to include amino acid analogs.

The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, and V.

The term "amino acid analog" refers to a molecule which is structurally similar to an amino acid and which can be substituted for an amino acid in the formation of a stapled peptide. Amino acid analogs include, without limitation, compounds which are structurally identical to an amino acid, as defined herein, except for the inclusion of one or more additional methylene groups between the amino and carboxyl group (e.g., a-amino ~-carboxy acids), or for the substitution of the amino or carboxy group by a similarly reactive group (e.g., substitution of the primary amine with a secondary or tertiary amine, or substitution or the carboxy group with an ester).

In one embodiment, at least one amino acid is functionalized (e.g. linked with a tetrazole moiety (referred to as a T-amino acid) and at least one amino acid is functionalized with an alkene moiety (referred to as an A-amino acid). An example of an alkene moiety is a methacrylic moiety. The tether connects the α-carbon of the functionalized amino acid and either, the tetrazole moiety or alkene moiety. In one embodiment, the tether is the amino acid side chain. In another embodiment, an amino acid side chain can be modified such that it is a tether. A peptide having functionalized amino acids incorporated therein is considered a functionalized peptide.

The functionalized peptides can include any combination of amino acids in addition to the functionalized amino acids. In one embodiment, a functionalized peptide can have from 2 to 32 amino acids (including at least two functionalized amino acids), including every integer from 2 to 32. For example, the functionalized peptide can have 7 or 12 amino acids.

The functionalized peptides of the invention can be prepared by any technique known to those skilled in the art or by techniques hereafter developed. For example, the peptides can be prepared using the solid-phase synthetic technique (Merrifield, J. Am. Chem. Soc., 15:2149-2154 (1963); M. Bodanszky et al., (1976) Peptide Synthesis, John Wiley & Sons, 2d Ed.; Kent and Clark-Lewis in Synthetic Peptides in Biology and Medicine, p. 295-358, eds. Alitalo, K., et al. Science Publishers, (Amsterdam, 1985). The synthesis of peptides by solution methods may also be used, as described in The Proteins, Vol. II, 3d Ed., p. 105-237, Neurath, H., et al., Eds., Academic Press, New York, N.Y. (1976). The synthesized peptides may be substantially purified by preparative high performance liquid chromatography or other comparable techniques available in the art. The composition of the synthetic peptides can be confirmed by any technique for amino acid composition analysis.

In one embodiment, a peptide of the invention has the amino acid sequence generally represented by the sequence Val Xaa Leu Gly Val Xaa Leu (SEQ ID NO:1), wherein the Xaa amino acids are a functionalized amino acid. Examples of such peptides are described in Example 2.

The functionalized peptide can be exposed to any wavelength of radiation which results in formation of the pyrazoline moiety. For example, a functionalized peptide (e.g., functionalized peptide of Structure I) or functionalized peptides can be exposed to ultraviolet radiation of from 300 to 320 nm, including all nanometers and 0.1 nanometers between 300 and 320, or microwave radiation of from 1.000 mm to 1.000 meter, including all millimeters and 0.1 millimeters between 1 mm and 1 meter. For example, the reaction is carried out in a Biotage microwave reactor using the manufacturer's recommended procedure.

Without intending to be bound by any particular theory, it is considered that on exposure to a suitable wavelength of electromagnetic radiation the tetrazole moiety undergoes a cycloreversion reaction to generate a nitrile imine dipole which reacts with a proximate alkene dipolarophile in a 1,3- or [3+2] cycloaddition reaction resulting in formation of a pyrazoline moiety.

Any peptide with a known primary amino acid sequence which contains a secondary structure believed to impart biological activity is a subject of the present invention. For example, for a peptide α-helical secondary structure, one surface of the helix (e.g., a molecular surface extending longitudinally along the axis of the helix and radially 45-135 degrees about the axis of the helix) may be required to make contact with another biomolecule in vivo or in vitro for biological activity. In such a case, the staple is designed to link two α-carbons of the helix while extending longitudinally along the surface of the helix.

The stapled peptides of the present invention include any peptide which comprises a pyrazoline moiety. For example, stapled peptides capable of adopting an α-helical structure may incorporate the pyrazoline moiety as part of an exogenous macrocyclic structure, where a portion of the macrocyclic structure is formed by the peptide. Such a peptide may be an α-helical peptide where two loops of a peptide helix are linked together by an exogenous macrocyclic structure formed at least in part by a pyrazoline moiety. As another example, the pyrazoline moiety may be incorporated in a peptide as part of a structure which links at least two peptides together. Such a peptide may have two peptide domains (either in single peptide or two peptides) which are connected by a linking structure comprising a pyrazoline moiety.

In one embodiment, the stapled peptides of the present invention include those represented by the following formula (Structure II):

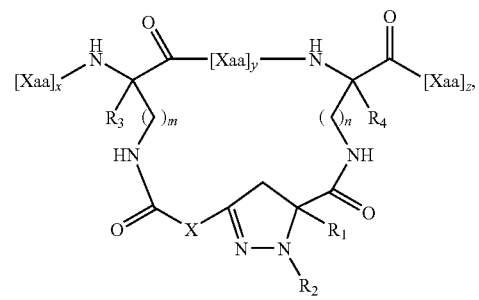

where the secondary structure of the peptide is α-helical. $R_1$ is H or an alkyl group with 1 to 6 carbons. $R_2$ is a phenyl group, a substituted phenyl group (such as alkoxy-, dialkylamino-substituted phenyl groups, and the like), or a heterocyclic group. $R_3$ is H or an alkyl group with 1 to 6 carbons. $R_4$ is H or alkyl group with 1 to 6 carbons. X is a phenyl group, substituted phenyl group, heterocyclic group, or a direct linkage between the carbonyl and tetrazole moieties. The number of carbons (e.g., methylene groups) comprising a tether between the α-carbon of the functionalized amino acid and either, the tetrazole moiety or alkene moiety, m or n, respectively, is independently 1 to 6. [Xaa] is any natural or synthetic amino acid. The number of amino acids in the peptide (in addition to the functionalized amino acids) is represented by x, y, and z, each of which can be from 1 to 10. The R groups (including the alkyl groups in any of the foregoing R groups, which can be linear or branched) can be substituted with functional groups such as halogens (including fluorine, chlorine, bromine, and iodine), alcohols, amines, ethers, esters, thiols, thioethers, thioesters, amides, and the like.

In one embodiment, the stapled peptide comprises an α-helix in aqueous solution.

The term "staple" as used herein refers to the intramolecular or intermolecular connection (also referred to as crosslinking) of two peptides or two peptide domains (e.g., two loops of a helical peptide). When the peptide has a helical secondary structure, the staple is a macrocyclic ring, which is exogenous (not part of) core or inherent (non-stapled) helical peptide structure. The macrocyclic ring is comprised of a pyrazoline ring and incorporates at least two amino acids of the peptide. The size of the macrocyclic ring is determined by the number of helical peptide amino acids (y) in the ring and the number methylene groups in the moieties connecting the pyrazoline group to the peptide (m and n). The stapled peptide has a least one peptide. In various embodiments, the stapled peptide has 1, 2, or 3 staples.

As used herein, the term "macrocyclic ring" refers to a ring or cycle formed by at least 10 covalently bonded atoms. As used herein, the term "stapled peptide" refers to a peptide comprising at least one pair of functionalized amino acids, wherein the functionalized amino acids are joined by a staple. In the case of a helical stapled peptide, the plurality of amino acids joined by a plurality of peptide bonds and at least one staple form a macrocyclic ring formed between the α-carbon of one amino acid and the α-carbon of another amino acid, which includes also any amino acid(s) between the functionalized amino acids.

The stapled peptide has at least one staple which comprises a pyrazoline moiety, which is a five-member, di-nitrogen heterocyclic ring. The pyrazoline moiety has three carbon atoms and two adjacent nitrogen atoms arranged in a five-member ring structure, and one double bond in the ring. For example, the pyrazoline moiety can be represented by the following structure:

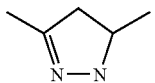

The pyrazoline ring can be substituted as represented by the following structure:

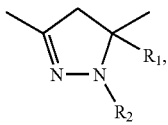

where $R_1$ is H or an alkyl groups with 1 to 6 carbons. $R_2$ is a phenyl group, substituted phenyl group (such as alkoxy-, dialkylamino-substituted phenyl groups, and the like), or a heterocyclic group. The pyrazoline ring can be fluorescent.

When the stapled peptide is a helical peptide, the pyrazoline ring is part of the exogenous macrocyclic ring which connects two loops of the α-helical peptide structure. For example, see the stapled peptide in FIG. 2. Preferably, the two connected loops are on the same face of the helix. For example, one amino acid of the helical peptide, which is the first amino acid incorporated in the macrocyclic ring, is defined as i. Each amino acid in the peptide is designated as a successive integer. Typically, the face of each successive loop is stapled by incorporating amino acids i to i+3, i+4, i+7, i+11, etc. in the macrocyclic ring, but the macrocyclic ring can incorporate any number of amino acids in the helical peptide up to 32. In one embodiment, the macrocyclic ring spans 1-, 2-, 3-, or 4-turns of the helix. In one embodiment, where a peptide has an amino acid sequence Xaa1, Xaa2, Xaa3, Xaa4, etc., the staple incorporates from $Xaa_1$ to $Xaa_4$, $Xaa_1$ to $Xaa_5$, $Xaa_1$ to $Xaa_8$, and $Xaa_1$ to $Xaa_{12}$.

Figure 3:
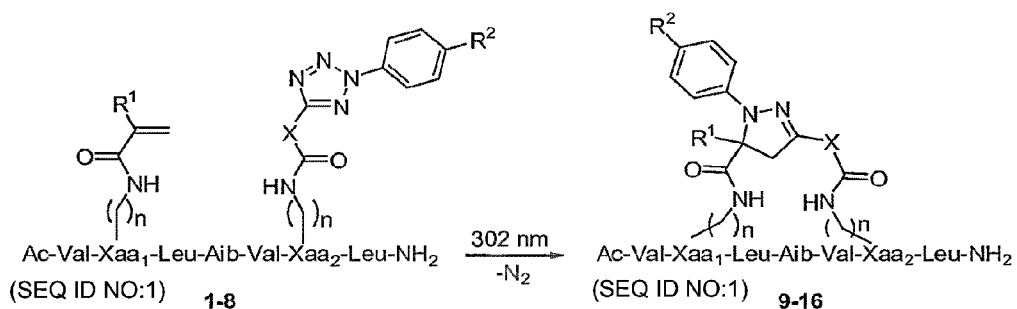
FIG. 3. Synthesis of stapled peptides based on the Karle and Balaram's eptapeptidic $3_{10}$-helix. Isolated yields are included.
Figure 8A:
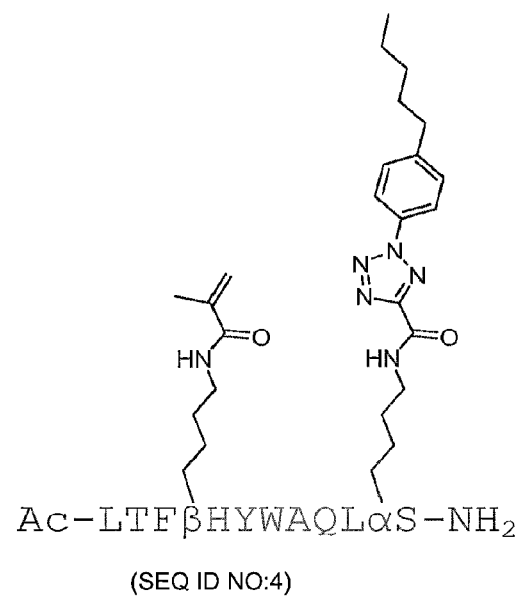
FIG. 8. UV-Vis and fluorescence spectra of the linear control peptide 18. Dashed lines represent the UV absorbance spectra while solid lines represent the fluorescence emission spectra. The absorption and emission maxima were marked on top of the spectra.
Figure 8A:
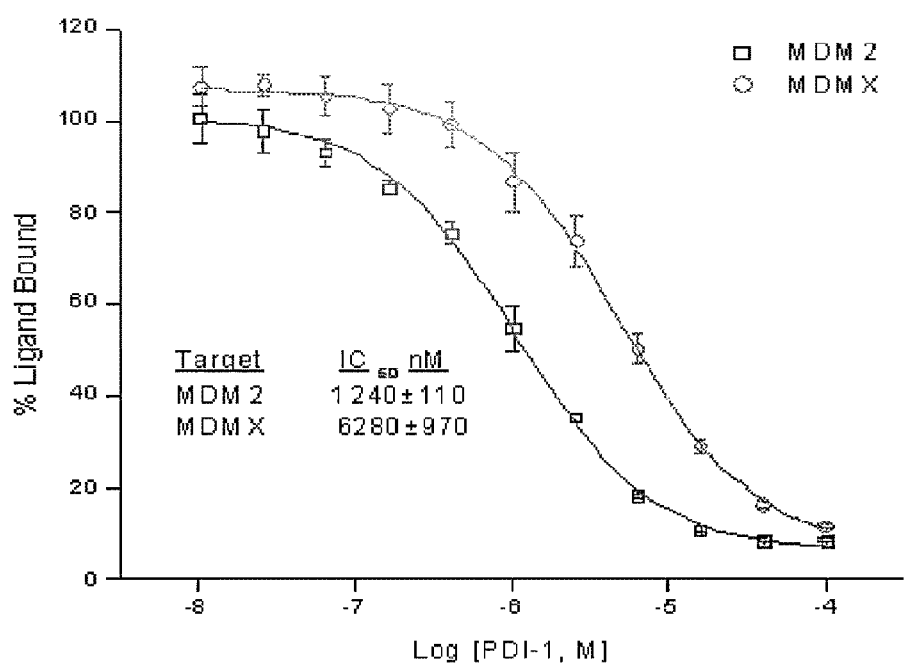
Figure 8B:
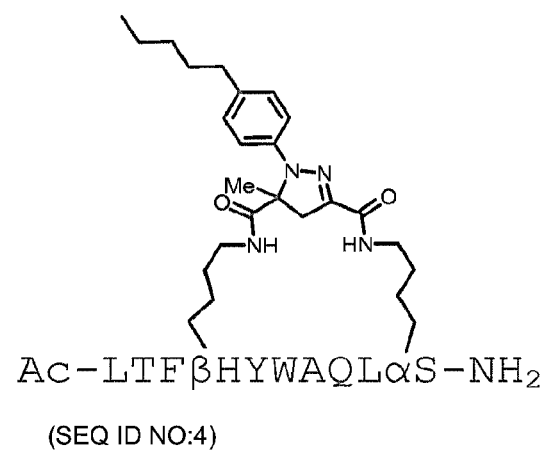
Figure 8B:
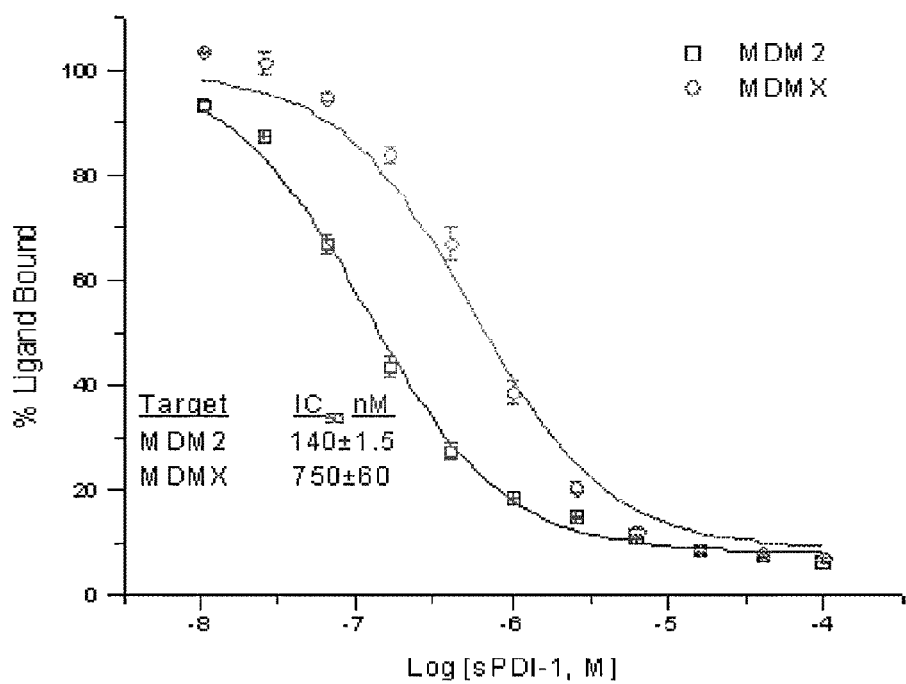
Figure 9:
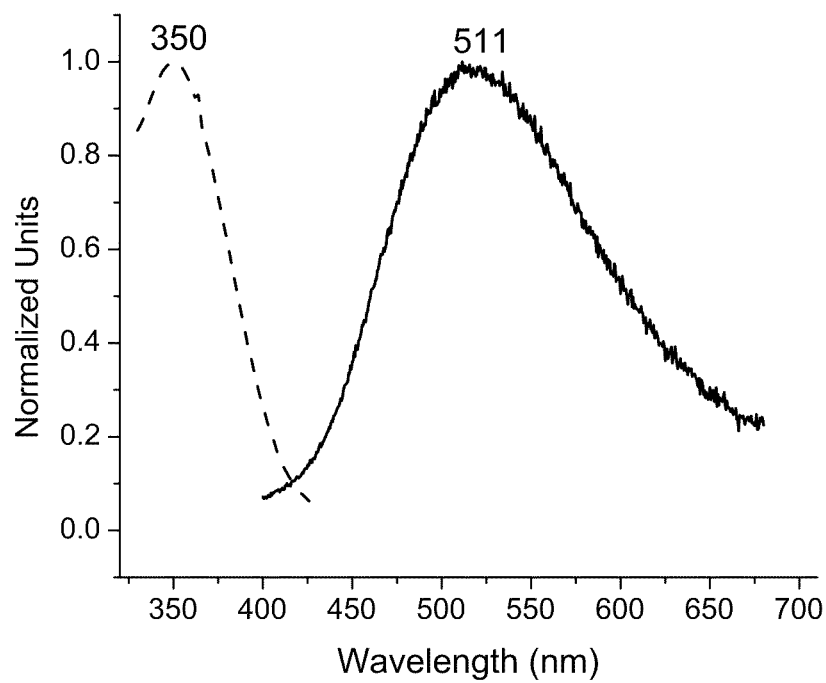
FIG. 9. UV-Vis and fluorescence data for peptide 18.
Figure 10:
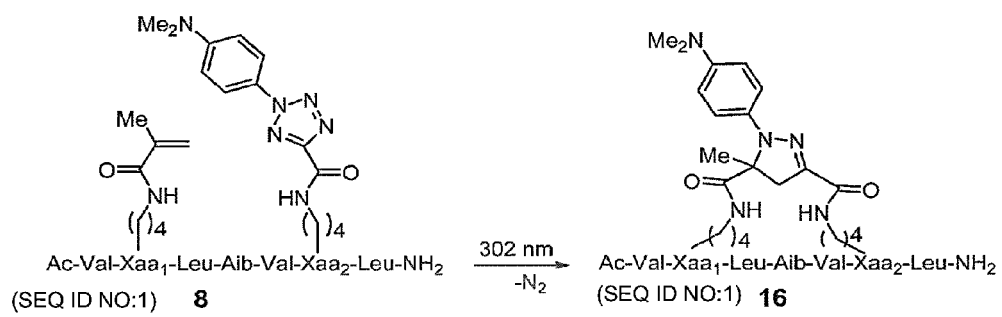
FIG. 10. Solvent compatibility data for stapled peptide preparation.

Illustrative functionalized peptides are shown in Example 1, FIG. 3 and FIG. 8(a). Illustrations of stapled peptides are shown in Examples 1 and 2, FIG. 3 and FIG. 8(a).

Stapled peptides of the present invention are prepared by exposure of a functionalized peptide to suitable electromagnetic radiation, and the preparation does not require additional chemical reactions or thermal treatment. The stapled peptides are free of detectable levels of metals (such as metals used in catalytic reactions (e.g. iron, copper, ruthenium, and the like). In one embodiment, the stapled peptides are free of chemicals or chemical reactants typically present in chemical reactions.

As used herein, the term "stability" refers to the maintenance of a defined secondary structure in solution by a stapled peptide, such as a stapled helical peptide, which can be measured by circular dichroism, NMR or another biophysical measure, or resistance to proteolytic degradation in vitro or in vivo. Non-limiting examples of secondary structures contemplated in this invention are α-helices, β-turns, and β-pleated sheets. As used herein, the term "helical stability" refers to the maintenance of a helical structure by a stapled helical peptide of the invention. In one embodiment, the helical stability can be measured by circular dichroism.

As used herein, the terms "increase" and "decrease" mean, respectively, to cause a statistically significant (i.e., p<0.1) increase or decrease of at least 5%.

In some embodiments, the stapled peptides of the present invention exhibit increased α-helical stability in aqueous solution compared to a corresponding non-stapled peptide. In other embodiments, the stapled peptide exhibits increased thermal stability compared to a corresponding non-stapled peptide. In yet other embodiments, the stapled peptide exhibits increased biological activity compared to a corresponding non-stapled polypeptide. In still other embodiments, the stapled peptide exhibits increased resistance to proteolytic degradation compared to a corresponding non-stapled peptide. In yet other embodiments, the stapled peptide exhibits increased ability to penetrate living cells compared to a corresponding non-stapled peptide.

Without wishing to be bound by a particular theory, it is considered that the stapled peptide may have increased overall hydrophobicity relative to a corresponding non-macrocyclic polypeptide. Also, the amide bond of the peptide backbone is susceptible to hydrolysis by proteases, thereby rendering peptidic compounds vulnerable to rapid degradation in vivo. It is considered that peptide helix formation, however, buries the amide backbone and therefore shields it from proteolytic cleavage.

In one embodiment, the stapled peptides exhibit improved biological properties, such as increased affinity for a target.

The α-helical content of each peptide can be calculated by dividing the mean residue ellipticity $[\phi]_{222obs}$ by the reported $[\phi]_{222obs}$ for a model helical peptide. For example, the stapled peptides of the present invention exhibit at least a 1.25, 1.5, 1.75 or 2-fold, including all 0.01-fold values between 1.25- and 2-fold, increase in α-helicity as determined by circular dichroism compared to a corresponding non-macrocyclic polypeptide.

In one embodiment, the stapled peptides exhibit increased thermal stability relative to a corresponding non-stapled peptide. For example, a stapled helical peptide can exhibit an increase in melting point $(T_m)$ of from 5 to 25° C., including all integers between 5 and 25° C. In various embodiments, the increase in melting point exhibited by the stapled peptide is at least 5, 10, 15, or 20° C.

In one aspect the present invention provides a method for transporting a helical peptide into a cell. In one embodiment, the method comprises the steps of: (a) providing a stapled peptide, and (b) contacting a cell with a composition comprising the stapled peptide, wherein a detectible fraction of the stapled peptide is transported into the cell. The detectible fraction of stapled peptide transported in a cell can be detected, for example, by optical fluorescence spectroscopy.

In another aspect, the present invention provides stapled peptides for treatment of an individual for a diseased state. The diseased state is one which can be affected by treatment with a composition comprising one or more stapled peptides of the present invention. An example of a diseased state is one which is affected by interaction of a stapled peptide with a cell, such that a gene or protein is up-regulated or down-regulated. In one embodiment, a therapeutic amount of a composition comprising a stapled peptide is administered to an individual to affect a diseased state.

For example, the PDI peptide sequence shown in Table 2 is known to inhibit the binding of MDM2 and MDMX to p53 (Baoli, et al. Cancer Res. 2007. Vol. 18, pp. 8810-8816). Thus, stapled peptides of the present invention having sequences such that they can inhibit the binding of MDM2 and MDMX to p53 can be used for modulating cell proliferation and/or differentiation.

For administration to an individual, compositions comprising the peptides according to the invention can be administered in a conventional dosage form prepared by combining the peptides with a standard pharmaceutically acceptable carrier according to known techniques. Some examples of pharmaceutically acceptable carriers can be found in: *Remington: The Science and Practice of Pharmacy* (2005) 21st Edition, Philadelphia, Pa. Lippincott Williams & Wilkins.

Various methods known to those skilled in the art may be used to introduce the peptides of the invention to an individual. These methods include but are not limited to intracranial, intrathecal, intradermal, intramuscular, intraperitoneal, intravenous, subcutaneous, oral, intranasal and retrograde routes.

It will be recognized by those with skill in the art that the form and character of the particular peptide dosing regime employed in the method of the invention will be dictated by the route of administration and other well-known variables, such as rate of clearance, the size of the individual and the stage of the particular disease or disorder being treated. Based on such criteria, one skilled in the art can determine an amount of any of the particular peptides described herein that will be effective to, for example, bind to or inhibit target proteins in the individual to achieve a desired result.

The following examples are presented to illustrate the present invention. They are not intended to be limiting in any manner.

Example 1

One example of stapled peptide helices based on an intramolecular photoactivated, nitrile imine-mediated 1,3-dipolar cycloaddition reaction ("photoclick chemistry") (FIG. 2) is discussed in the following.

We observed that the nitrile imine species, while reactive toward suitable alkenes, was exceedingly stable in the aqueous medium. To probe whether this unique reactivity profile can be harnessed to "staple" peptides, we appended an alkene and a tetrazole moiety, respectively, to peptide side chains located at the i and i+4 positions of Balaram's $3_{10}$-helix (scheme in FIG. 3). We chose this peptide helix model because it has been studied previously by Grubbs and co-workers in demonstrating ruthenium-catalyzed ring closing metathesis chemistry for peptide stapling. We envisioned that upon photoirradiation, tetrazole would undergo the cyclorversion reaction to generate the nitrile imine dipole in situ, which would then react with a proximal alkene dipolarophile to form a fluorescent pyrazoline cross-linker.

To examine conformational effect on the reaction efficiency, we prepared a series of linear peptide precursors (1-8) by attaching various alkene and tetrazole moieties, respectively, at the side chains of either lysines or ornithines located at the 2- and 6-positions (FIG. 3). To affect macrocycloaddition, the linear peptides (150 μM in acetonitrile) were photoirradiated with a 302-nm handheld UV lamp (UVM, 0.16 AMPS) for 2 hours and the resulting stapled peptides were purified by reverse-phase HPLC. Interestingly, we found: 1) the lysine side chains gave higher yields than the ornithine side chains (compare peptides 3-8 to 1-2), suggesting that larger rings cause less strains and therefore are more conducive to the macrocycloaddition reactions; 2) N-(4-methoxy)- and N-(4-dimethylamino)-phenyl tetrazoles gave higher yields than simple N-phenyl tetrazole (compare 6 and 8 to 3), which can be attributed to higher reactivities of the corresponding nitrile imines; 3) linear peptide 8 carrying methacrylic and N-(4-dimethylamino) phenyl tetrazole side chains afforded the highest yield (94%), suggesting that both the tetrazole reactivity and the alkene conformational rigidity (methacrylic vs. acrylic) are important for the macrocycloaddition reaction; and 4) the stapling reaction involving peptide 8 was found to be tolerant of protic solvents such as EtOH and iPrOH as well as EtOH/H$_2$O (1:1) mixture, affording similar yields (see FIG. 11). Additionally, a preliminary study with a p53 analog, Ac-LTFαHYWAQLβS-NH2 (SEQ ID NO:4) where α and β represent methacrylic and N-(4-methoxy) phenyl-tetrazole modified lysine, respectively, showed that the cyclized product was isolated in 74% yield, indicating that the stapling is compatible with the polar side chains.

Figure 5A:
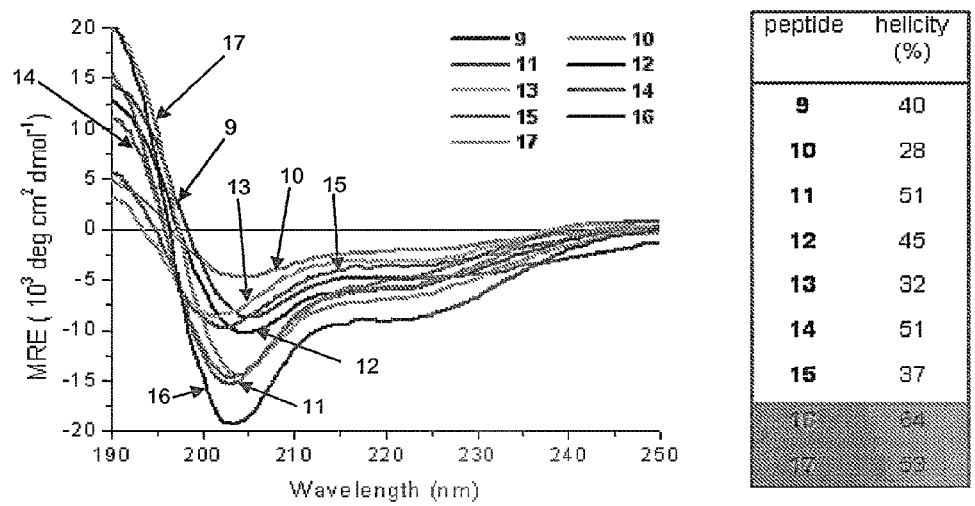
FIG. 5. (a) CD spectra of the stapled peptides 9; 10; 11; 12, 13, 14, 15 and 16, and the control linear peptide 17. Peptides were dissolved in TFE to derive 100 µM solutions. The samples were scanned from 190 nm to 250 nm with a bandwidth of 1 nm. (b) Thermal melting curves of peptides 16 and 17.
Figure 5B:
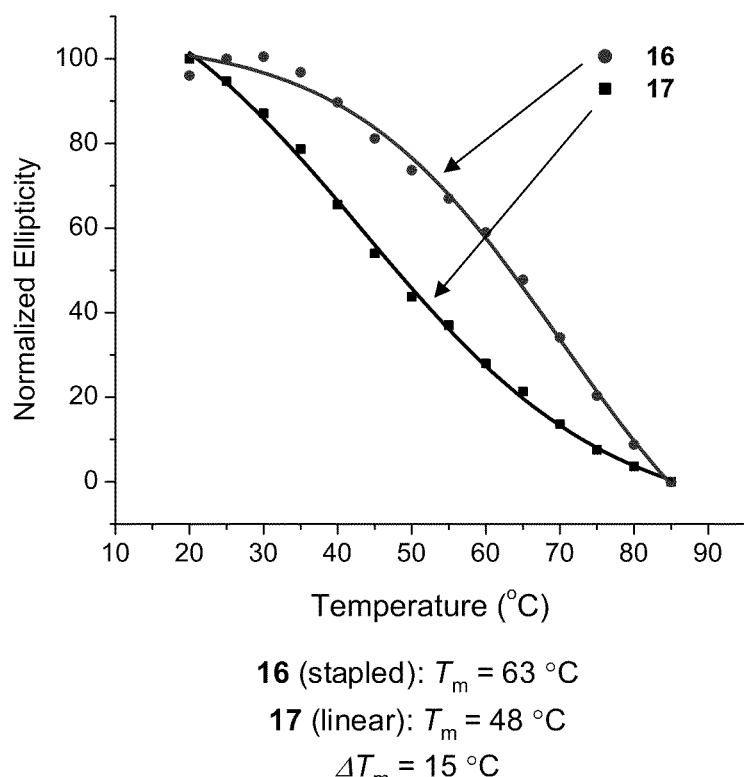
Figure 6:
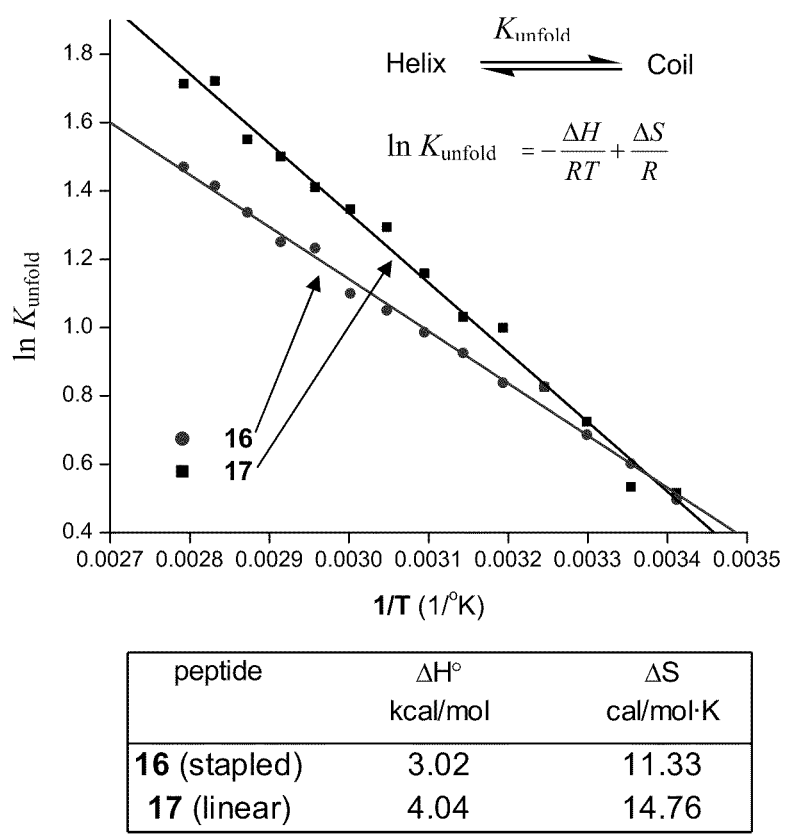
FIG. 6. Fluorescence and optical imaging data for stapled peptide cell permeability.

To examine the stapling effect on peptide secondary structure, we measured the far-UV circular dichroism (CD) spectra of the stapled peptides in trifluoroethanol (TFE) at 25° C. Because the tetrazoles in the linear peptides are labile to the CD scanning light (short wavelength UV light), we prepared a photo stable control peptide, Ac-Val-Lys(Ac)-Leu-Aib-Val-Lys(Ac)-Leu-NH2 (SEQ ID NO:1) (17; Ac=acetyl; Aib=amino isobutyric acid) as a linear surrogate. Peptide 17 showed typical CD spectrum of a right-handed $3_{10}$-helix with a strong negative band around 208 nm (π→π*) and a weak negative band around 222 nm (n→π*) (FIGS. 5 (a) and (b)). The percent helicity of 17 was determined to be 53% on the basis of mean residue ellipticity (MRE) at 208 nm. By comparison, stapled peptides 11 and 14 showed similar percent helicity (51% for both) while 16 exhibited slightly higher percent helicity (64%) (FIG. 5(a)), indicating that the methyl group attached to the pyrazoline rings reinforces the helical structures. To further characterize the stability derived from the stapling, we measured thermal melting point ($T_m$) of the most helical peptide 16 by following its ellipticity over a wide temperature range (20-85° C.), and compared it to that of the linear photo stable peptide 17 (FIG. 5 (b)). We found that stapled peptide 16 exhibited higher melting temperature ($T_m$=63° C.) than linear peptide 17 ($T_m$=48° C.); the 15° C.-increase is greater than 10° C.-increase observed for a double cysteine alkylation cross-linker spanning the i and i+11 positions of an α-helical peptide, suggesting that helical reinforcement afforded by the pyrazoline cross-linker is robust.

Figure 2:
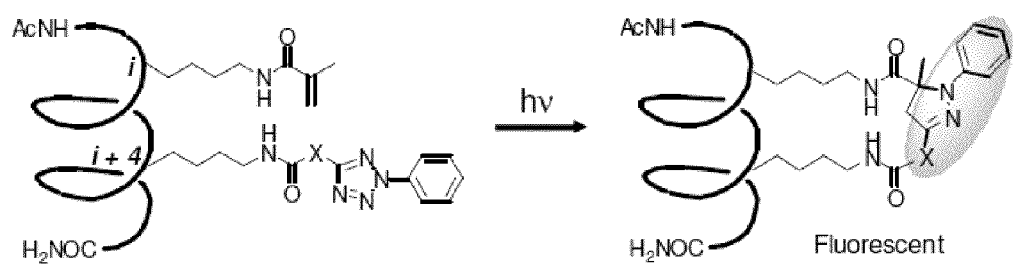
FIG. 2. A peptide stapling strategy based on intramolecular photoclick chemistry: X represents a spacer.
Figure 4:
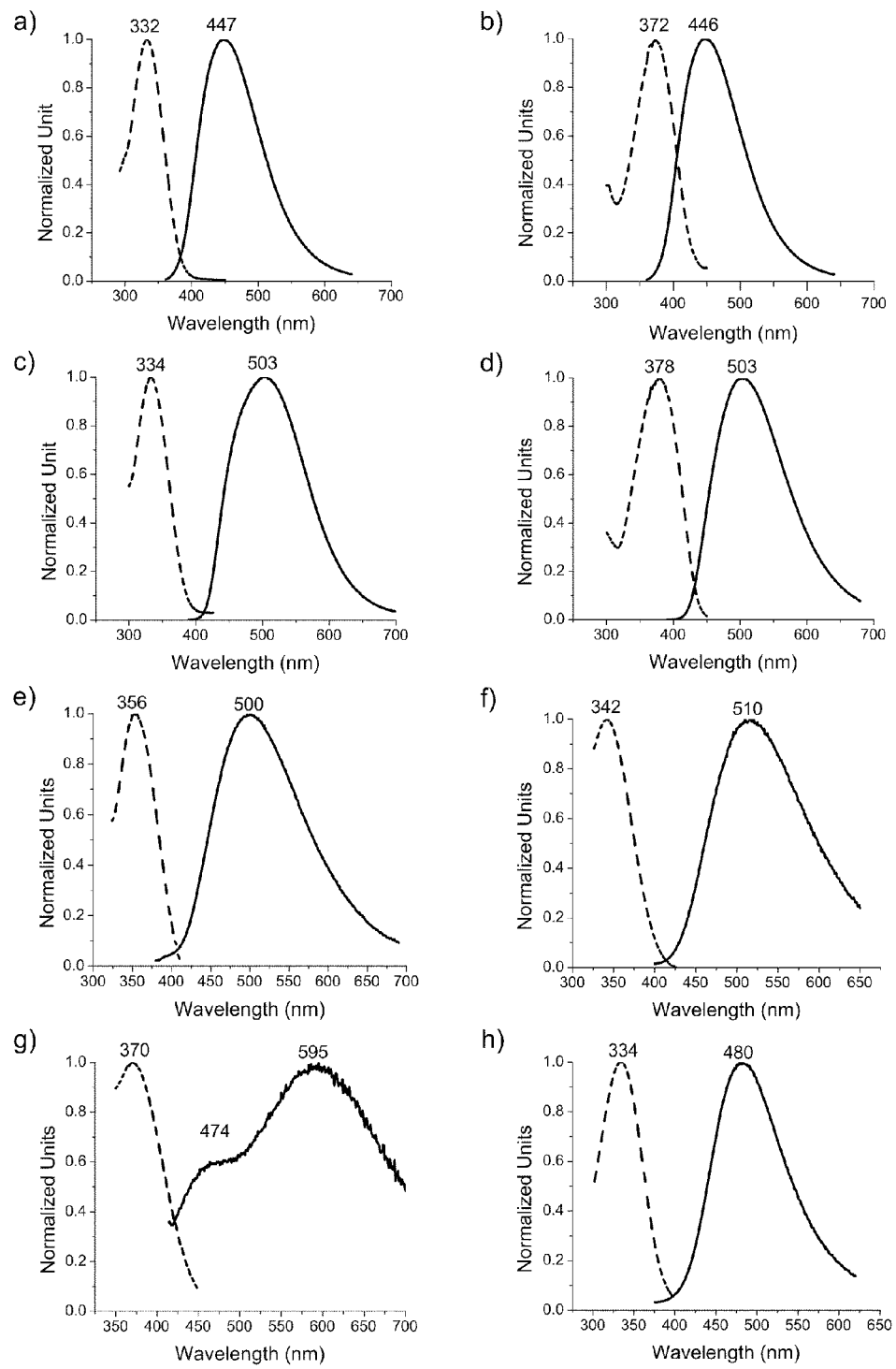
FIG. 4. UV-Vis and fluorescence spectra of the stapled peptides: (a) 9; (b) 10; (c) 11; (d) 12, (e) 13, (f) 14, (g) 15, (h) 16. Dashed lines represented UV absorbance spectra and solid lines represent fluorescence emission spectra. The absorption and emission maxima were marked on top of the spectra.

Since pyrazoline crosslinkers are fluorescent, we measured the UV and fluorescence spectra of the eight stapled peptides (FIG. 2). As expected, large Stokes shifts (74~169 nm) were observed, in excellent agreement with our previous observation. In general, it appears that the strained, stapled peptides with lower percent helicity (see FIG. 5(a)) showed consistently smaller Stokes shifts compared to their relaxed counterparts (compare 10 to 9, 12 to 11, and 13 to 14) (FIG. 4). Since Stokes shift reflects the electronic displacement in potential surfaces between the ground and excited states of the chromophore, the decreases in Stokes shift observed in 10, 12, and 13 can be attributed to the rigidified ground states and thus increased potential surfaces—the result of macrocyclic ring strains.

Figure 7:
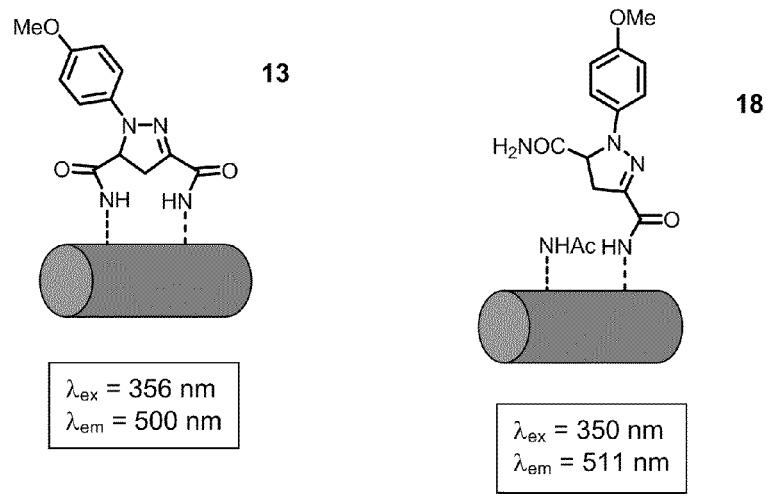
FIG. 7. Representative ELISA assay plots: (a) unstapled peptide, PDI-1; (b) sPDI-1.
Figure 7:
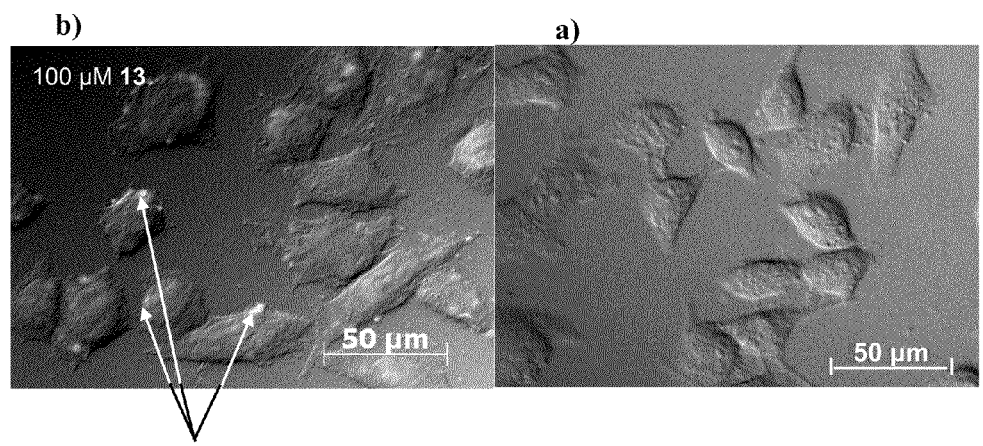

To assess whether the stapled peptides are capable of penetrating cell membrane, we took advantage of the intrinsic fluorescence of the pyrazoline cross-linkers and monitored the stapled peptide cellular uptake by fluorescent microscopy. Because stapled peptide 13 showed maximum absorption at 356 nm and a broad emission band at 400-700 nm (FIG. 4(e)), matching closely to commercial DAPI filter settings (ex 365 nm, em 445±25 nm), we decided to use peptide 13 in our cellular uptake assay. After incubating HeLa cells with 100 µM of peptide 13 for 4 hours in a 37° C. $CO_2$ incubator, the cells were washed twice with PBS before fixing with 4% paraformaldehyde and the subcellular distribution of peptide 13 was examined by fluorescent microscopy. Interestingly, punctuated fluorescence was observed in discrete cytoplasmic regions within HeLa cells (FIG. 7, see arrows indicating examples of intracellular fluorescence), resembling closely the intracellular distribution pattern of the hydrocarbon-stapled BH3 helix, which in turn suggests that the pyrazoline stapled peptides penetrates cell membrane via a similar pinocytotic pathway. In a control experiment, treatment of HeLa cells with a linear analog 18 (Ac-Val-Lys(Pyr)-Leu-Aib-Val-Lys(Ac)-Leu-NH2; Pyr=pyrazoline fluorophore with the same structure as that of peptide 13) did not yield cellular fluorescent pattern under the identical conditions (FIG. 7(b)), suggesting that the membrane permeation is indeed endowed by the side chain stapling.

In summary, we have demonstrated a facile synthesis of stapled peptide helices using a photoinduced, nitrile imine-mediated, intramolecular 1,3-dipolar cycloaddition reaction. When appropriate alkenes and tetrazoles were employed, high stapling yields were obtained along with the reinforced helical structures. Moreover, one stapled peptide was found to be capable of permeating the HeLa cell membrane. With this new orthogonal stapling reaction, it might be possible to combine several orthogonal reactions to design novel, multiply stapled peptide structures. By taking advantage of the spatiotemporal resolution of light activation, it is also possible to "switch-on" the biologically active form of a peptide in specific cell types.

Materials and General Procedures

General Methods: $^1$H-NMR spectra were recorded on either an Inova 500 MHz NMR instrument or an Inova 400 MHz NMR instrument. Chemical shifts were reported in parts per million (ppm) relative to internal solvent standards. Multiplicities were reported as follows: singlet (s), doublet (d), triplet (t), doublet of doublet (dd), quintet (q) or multiplet (m). UV-Vis Data were recorded using a HP 8452 Diode Array Spectrophotometer monitoring from 195-825 nm. Fluorescence measurements were conducted using 1-cm pathlength cuvettes on JY Fluorolog spectrofluorimeter at 20° C. Fluorescence emission was scanned in the range of 400 to 700 nm through a 2-nm slit. Low-resolution LC-MS spectra were recorded using a Thermo Finnigan LCQ Advantage instrument operating in the positive ion mode. High-resolution ESI-MS analysis was performed by SUNY Buffalo Instrument Center.

HPLC Purification and Analysis: Purification of linear peptides was conducted using silica gel flash chromatography. Cyclic peptides were purified using a Gilson reverse-phase HPLC system and a semi-prep Phenomenex $C_{18}$ column with a flow rate set to 5 mL/min and a gradient of 10-90% ACN/$H_2O$ while monitoring at 220 nm and 370 nm. HPLC analyses were carried out using an analytical Gilson RP-HPLC system and a Keystone Scientific $C_{18}$ column monitoring at 254 nm.

Circular Dichroism: CD spectra were obtained using 1-mm pathlength cuvettes on a JASCO J-715 instrument at 25° C. The instrument scan range was set at 190 to 250 nm. The scan rate was set at 50 nm/min, the response time was set at 2 sec, and the bandwidth was set at 1 nm. The spectra were the averages of two scans. For the measurement of percent helicity, peptides were dissolved in 100% trifluoroethanol (TFE); for the $T_m$ determination, 20% TFE/$H_2O$ were used as the solvent. The percent helicity was calculated by using the following equation:

$$\% \text{ helicity} = \frac{[\theta]_{208\ MRE} - 4000}{-29000} \times 100.$$

The melting temperature ($T_m$) was determined by following a reported procedure. Briefly, a sample of 100 µM peptide in 20% TFE/$H_2O$ in an 1-mm pathlength cuvette was scanned at various temperatures from 20° C. to 85° C. (5-degree intervals) with an equilibration time of 3 min and a heating rate of 60° C./hr. The $\theta_{222\ MRE}$ data was normalized by setting the maximum $\theta_{222\ MRE}$ to 100% and the minimum $\theta_{222\ MRE}$ to 0.

Solid Phase Peptide Synthesis. Linear peptides were synthesized by following standard 9H-fluoren-9-yl-methoxycarbonyl (Fmoc) solid phase peptide synthesis protocol with Rink-amide resin using a Protein Technologies Tribute Synthesizer. Briefly, five equiv. of HBTU, five equiv. of amino acids, and ten equiv. of NMM in DMF were used in each coupling reaction. The coupling reaction was allowed to proceed for 45 minutes. The Fmoc deprotection was accomplished by treating the resin-bound peptides with 20% piperidine/DMF (2×, 10 min each). Fmoc-Lys(alkene)-OH and Fmoc-Lys(tetrazole)-OH were used as in the assembly of the linear peptides. The acylation of the linear peptides was accomplished by treating the resin with 20 equiv. of acetic anhydride and 30 equiv. of DIEA in DCM for 1 hour.

Photoactivated Synthesis of Stapled Peptides. The linear peptides were cleaved from the Rink amide resin by treating the resin with a cleavage cocktail containing 95% TFA, 2.5% triisopropylsilane, and 2.5% water for 1.5 hours. The acidic solution was added to diethyl ether and the peptide was collected by centrifugation. The peptide was washed with diethyl ether and dried under high vacuum, giving the crude peptide with 20-40% yield based on the resin substitution. The crude peptide was then purified by a preparative reverse-phase HPLC. Following purification and lyophilization, the linear peptide was dissolved in acetonitrile/$H_2O$ (95:5) to generate an 150 µM solution. The solution was irradiated with 302-nm light using a handheld UV lamp (UVP, Model UVM-57) for two hours. Following irradiation the material was purified by a preparative reverse-phase HPLC to give the stapled peptides, generally in 10-15% overall yield based on resin substitution.

Microwave Synthesis of Stapled Peptides. The linear peptides (50 µmol) on the Rink amide resin were placed in a Biotage microwave reaction vial in 2.5 mL NMP and placed in a Biotage microwave reactor. The reaction mixture was heated to 200° C. for 12 minutes. Following reaction the cyclic peptides were washed 5 times with DCM and once with methanol prior to cleavage. The peptide was cleaved from the Rink amide resin by treating the resin with a cocktail containing 95% TFA, 2.5% triisopropylsilane, and 2.5% water for 1.5 hours. The acidic solution was added to diethyl ether and the precipitated peptide was collected by centrifugation. The peptide was washed again with diethyl ether and dried under high vacuum. The purification was carried out in a preparative reverse-phase HPLC and gave the stapled peptide with ~1% overall yield based on resin substitution.

Synthesis and Characterization of Linear and Cyclic Peptides

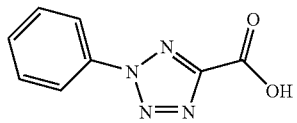 [SMILES: O=C(O)c1nnn(-c2ccccc2)n1]

2-Phenyl-2H-tetrazole-5-carboxylic acid: To 0.8 mL ethyl glyoxylate in toluene (50%) was added 130 mL ethanol solution of sulfonyl hydrazide (0.69 g, 4.0 mmol). The resulting mixture was stirred for 1 hr at room temperature in an open flask before 130 mL of chilled distilled water was added. A white precipitate (sulfonylhydrazone) was generated, which was collected by filtration. The filtrate was subsequently dissolved in 50 ml pyridine to derive solution A. Separately, to a 10 mmol solution of aniline in a 1:1 mixture of ethanol and water (20 mL cooled to −5° C.) was added 3.0 mL of concentrated HCl. To the resulting acidic aniline solution, 4 mL solution of sodium nitrate (0.690 g, 10 mmol) was added drop-wise generating the phenyl-diazonium salt solution (solution B). Both solutions were cooled to −5° C. and solution B was added drop-wise to solution A over a period of 30 minutes. Following addition, the reaction mixture was allowed to warm up to room temperature over 45 min and subsequently extracted with ethyl acetate three times. The organic layer was subsequently washed with a 0.1 N HCl solution, dried over sodium sulfate, and concentrated. The crude mixture was purified via a silica gel chromatography using a stepwise gradient of ethyl acetate/hexane to afford ethyl 2-phenyl-2H-tetrazole-5-carboxylate as a pink-purple powder. Following purification, sodium hydroxide (7.5 mmol; 0.6 g dissolved in 2 mL of water) was added to a 50 mL solution of ethyl 2-phenyl-2H-tetrazole-5-carboxylate in ethanol. The reaction mixture was refluxed overnight and allowed to cool to −5° C. The mixture was acidified with 1.2 mL of dilute HCl solution. The resulting solution was extracted five times with ethyl acetate to yield the titled compound (0.37 g, 49%): $^1$H NMR (500 MHz, CDCl$_3$) δ 8.24 (d, J=7.5 Hz, 2H) 7.60 (m, 3H); $^{13}$C NMR (75.4 MHz, CDCl$_3$) δ 158.6, 158.3, 135.9, 130.7, 130.2, 120.3; HRMS (EI) calcd for C$_8$H$_6$N$_2$O$_2$ 162.0424 [M−N$_2$]$^+$, found 162.0423.

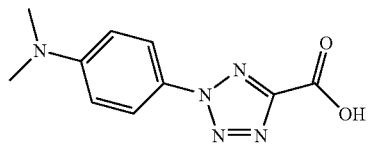 [SMILES: CN(C)c1ccc(-n2nnc(C(=O)O)n2)cc1]

2-(4-Dimethylamino-phenyl)-2H-tetrazole-5-carboxylic acid: To 1.6 mL of ethyl glyoxilate in toluene was added 130 mL ethanol solution of sulfonyl hydrazide (1.38 g, 8.0 mmol). The resulting mixture was stirred for 1 hr at room temperature in an open flask before being quenched by addition of ice. A white precipitate (sulfonylhydrazone) was formed, and collected by filtration. The filtrate was subsequently dissolved in 50 ml of pyridine to derive solution A. Separately, to a 7.2 mmol solution of N,N-dimethylamino aniline in a 3:1 mixture of ethanol and water (20 mL, cooled to −5° C.) was added 3.0 mL of concentrated HCl. To the resulting acidic aniline solution, 4 mL solution of sodium nitrite (0.690 g, 10 mmol) was added drop wise to derive the phenyl diazonium salt solution (solution B). Solution A was cooled to −20° C. and solution B (kept at −5° C.) was added drop wise to solution A over a period of 30 minutes. Following addition, the reaction mixture was allowed to warm up to room temperature over 60 min and subsequently extracted with ethyl acetate three times. The organic layer was washed with 0.1 N HCl, dried over sodium sulfate, and concentrated. The crude mixture was purified by silica gel chromatography using a stepwise gradient of ethyl acetate/hexane to afford 2-(4-dimethylamino-phenyl)-2H-tetrazole-5-ethyl ester as a blue green powder. Following purification, sodium hydroxide (0.6 g, 7.5 mmol, dissolved in 2 mL water) was added to a 50 mL solution of 2-(4-dimethylamino-phenyl)-2H-tetrazole-5-ethyl ester in ethanol. The mixture was refluxed for 2 hrs and allowed to cool to room temperature. The mixture was acidified with a dilute HCl solution, and the solution was extracted three times with ethyl acetate to yield the titled compound (0.39 g, 23%): $^1$H NMR (500 MHz, DMSO-d$_6$) δ 7.88 (d, J=9.0 Hz, 2H), 6.89 (d, J=9.0 Hz, 2H), 3.01 (s, 6H); $^{13}$C NMR (75.4 MHz, DMSO-d$_6$) δ 158.8, 157.7, 151.4, 125.0, 121.4, 121.3, 112.0, 39.8; HRMS (ESI) calcd for C$_{10}$H$_{12}$N$_5$O$_2$ 234.0986 [M+H$^+$], found 234.0987.

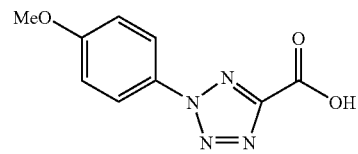 [SMILES: COc1ccc(-n2nnc(C(=O)O)n2)cc1]

2-(4-Methoxy-phenyl)-2H-tetrazole-5-carboxylic acid: To 1.6 mL of ethyl glyoxilate in toluene was added 130 mL ethanol solution of sulfonyl hydrazide (1.38 g, 8.0 mmol). The resulting mixture was stirred for 1 hour at room temperature in an open flask before being pored over 100 g of ice. A white precipitate (sulfonylhydrazone) was generated, which was collected by filtration. The filtrate was subsequently dissolved in 50 mL pyridine to derive solution A. Separately, to a 7.2 mmol solution of 4-methoxy-aniline in a 3:1 mixture of ethanol and water (20 mL cooled to −5° C.) was added 3.0 mL of concentrated HCl. To the resulting acidic aniline solution, 4 mL solution of sodium nitrite (0.690 g, 10 mmol) was added drop wise to generate the phenyldiazonium salt (solution B). Solution A was cooled to −20° C. and solution B (kept at −5° C.) was added drop wise to solution A over a period of 30 minutes. Following addition, the reaction mixture was allowed to warm up to room temperature over 60 minutes and subsequently extracted with ethyl acetate three times. The organic layer was then washed with 0.1 N HCl, dried over sodium sulfate, and concentrated. The crude mixture was purified via a silica gel chromatography using a stepwise gradient of ethyl acetate/hexane to afford 2-(4-methoxy-phenyl)-2H-tetrazole-5-ethyl ester as a light yellow-brown powder. Following purification, sodium hydroxide (7.5 mmol; 0.6 g dissolved in 2 mL of water) was added to a 50 mL solution of 2-(4-methoxy-phenyl)-2H-tetrazole-5-ethyl ester in ethanol. The mixture was refluxed for 2 hrs before cooling down to room temperature. The mixture was acidified with a dilute HCl solution. The resulting 2-(4-methoxy-phenyl)-2H-tetrazole-5-carboxylic acid was extracted three times with ethyl acetate to yield the titled compound (0.55 g, 35%): $^1$H NMR (500 MHz, DMSO-$d_6$) δ 8.02 (d, J=9.5 Hz, 2H), 7.20 (d, J=8.5 Hz, 2H), 3.85 (s, 3H); $^{13}$C NMR (75.4 MHz, DMSO-$d_6$) δ 158.6, 160.4, 159.1, 129.7, 121.8, 115.3, 115.0, 55.8, 55.6; HRMS (EI) calcd for $C_9H_8N_2O_3$ 192.0529 [M-$N_2$]$^+$, found 192.0531.

treating the resin with 20 equiv of methacrylic anhydride and 30 equiv of DIEA in DCM for 1 hour. The peptides were cleaved from the Rink amide resin by treating the resin with a cleavage cocktail containing 95% TFA, 2.5% triisopropylsilane, and 2.5% water for 1 hour. The filtrates were concentrated and then extracted with DCM. The organic layer was washed 3× with saturated sodium bicarbonate solution, concentrated, and dried under high vacuum. The crude peptides were purified by either silica gel flash chromatography or preparative HPLC.

General Procedure for Photoinduced Peptide Stapling: A stirred solution of linear peptide (150 μM, dissolved in HPLC-grade acetonitrile) in a quartz round-bottom flask was irradiated with a 302-nm UV lamp (UVM-57, 302 nm, 115V, 0.16 AMPS) under argon for 2 hours. The solution was concentrated and the crude product was purified by preparative RP-HPLC. The fractions that showed greater than 95% purity with the correct masses were pooled and lyophilized to give the stapled peptide as a fluffy white powder.

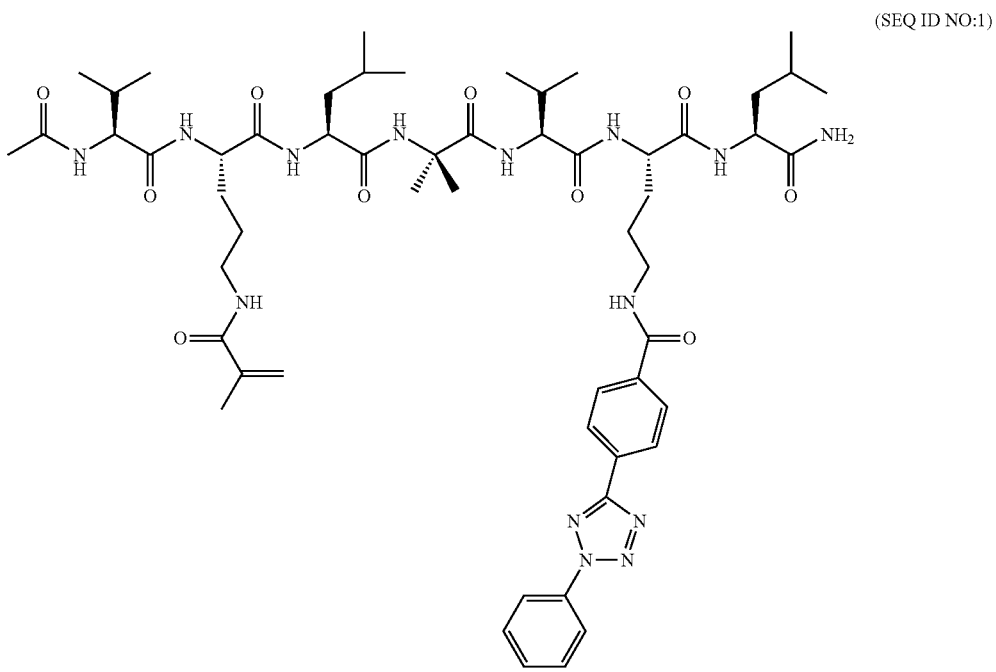

(SEQ ID NO:1)

Solid Phase Peptide Synthesis: Linear peptides were synthesized by following standard 9H-fluoren-9-yl-methoxycarbonyl (Fmoc) solid phase peptide synthesis protocol on the Rink-amide resin. Briefly, three equiv of HBTU/HOBt, three equiv of amino acids, and six equiv of DIEA in DMF were used in each coupling reaction. The coupling reaction was allowed to proceed for 40 minutes. The Fmoc deprotection was accomplished by treating the resin-bound peptides with 20% piperidine/DMF (2×, 10 min each). Fmoc-Lys(Mtt)-OH and Fmoc-Orn(Mtt) were used as in the assembly of the peptides. The selective removal of Mtt was accomplished by treating the resin with 1% TFA/DCM (5×, 10 min each). The coupling of the tetrazole to the deprotected Lys/Orn side chain was achieved by treating the resin with 3 equiv of HBTU/HOBT, 3 equiv of tetrazole, and 6 equiv of DIEA in DCM/DMF (1:1) for 1 hour. The coupling of methacrylic acid to the deprotected Lys/Orn side chain was carried out by Linear Peptide (1) (SEQ ID NO:1): Heptapeptide 1 was prepared according to the general procedure. After purification, a yellow-white crystalline solid was obtained in 7% yield (based on resin substitution): $^1$H-NMR (CD$_3$OD, 500 MHz) δ 8.18 (d, J=7.8 Hz, 2H), 7.65 (t, J=8.0 Hz, 2H), 7.62 (d, J=7.2 Hz, 1H), 5.69 (d, J=14.0 Hz, 1H), 5.37 (d, J=16.8 Hz, 1H), 4.37 (d, J=7.7 Hz, 1H), 4.18-4.08 (br, m, 3H), 3.98 (t, J=6.6 Hz, 1H), 3.89 (d, J=6.8 Hz, 1H), 3.81 (d, J=7.3 Hz, 1H), 3.63 (t, J=5.9 Hz, 1H), 3.56-3.45 (br, m, 1H), 3.23 (br, m, 1H), 2.23 (br, m, 1H), 2.09 (s, 3H), 2.05 (s, 1H), 2.01-1.96 (br, m, 1H), 1.93 (s, 1H), 1.89 (s, 1H), 1.79-1.59 (br, m, 10H), 1.50 (s, 3H), 1.47 (s, 2H), 1.44 (s, 3H), 1.37-1.28 (br, m, 2H), 1.07-0.85 (br, m, 24H); HRMS (ESI) calcd for $C_{50}H_{80}N_{14}O_{10}Na$ 1059.6074 [M+Na$^+$], found 1059.6069.

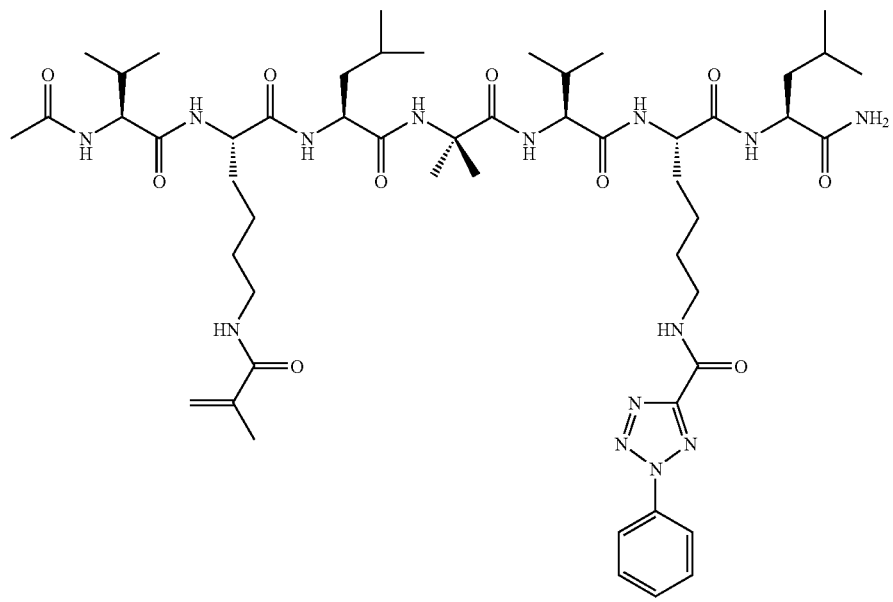

Linear Peptide (2) (SEQ ID NO:1): Heptapeptide 2 was prepared according to the general procedure. After purification, a yellow-white crystalline solid was obtained in 10% yield (based on resin substitution): $^1$H-NMR (CD$_3$OD, 400 MHz) δ 8.31 (d, J=8.2 Hz, 2H), 8.22 (d, J=7.8 Hz, 2H), 7.66 (t, J=7.8 Hz, 2H), 7.59 (t, J=7.3 Hz, 1H), 5.66 (s, 1H), 5.32 (s, 1H), 4.37 (dd, J=7.5, 4.0 Hz, 1H), 4.17 (t, J=5.0 Hz, 2H), 4.11 (t, J=7.9 Hz, 1H), 3.93 (d, J=6.6 Hz, 1H), 3.83 (d, J=6.7 Hz, 1H), 3.48 (br, m, 2H), 3.24 (m, 2H), 2.23 (m, 2H), 2.07 (s, 3H), 1.99 (br, m, 3H), 1.89 (s, 3H), 1.77 (br, m, 4H), 1.63 (br, m, 6H), 1.49 (s, 3H), 1.45 (s, 3H), 1.19 (br, m, 1H), 1.07-0.99 (br, m, 13H), 0.96-0.90 (br, m, 13H); HRMS (ESI) calcd for C$_{56}$H$_{84}$N$_{14}$O$_{10}$Na 1135.6387 [M+Na$^+$], found 1135.6375.

Linear Peptide (3): Heptapeptide 3 was prepared according to the general procedure described above. After purification, a yellow-white crystalline solid was obtained in 25% yield (based on resin substitution): $^1$H-NMR (CD$_3$OD, 500 MHz) δ 8.17 (d, J=7.3 Hz, 2H), 7.65 (t, J=7.0 Hz, 2H), 7.61 (d, J=7.1 Hz, 1H), 5.67 (d, J=11.3 Hz, 1H), 5.33 (d, J=8.8 Hz, 1H), 4.38 (m, 1H), 4.12 (m, 3H), 3.92 (d, J=6.7 Hz, 1H), 3.80 (d, J=7.2 Hz, 1H), 3.48 (m, 2H), 3.22 (t, J=6.7 Hz, 2H), 2.21 (m, 1H), 2.14 (s, 1H), 2.07 (s, 3H), 1.89 (br, m, 5H), 1.86-1.63 (br, m, 11H), 1.55 (br, m, 2H), 1.49 (s, 3H), 1.44 (s, 3H), 1.24-1.18 (br, m, 1H), 1.06-0.84 (br, m, 26H); HRMS (ESI) for C$_{52}$H$_{84}$N$_{12}$O$_{10}$Na 1087.6387 [M+Na$^+$], found 1087.6417.

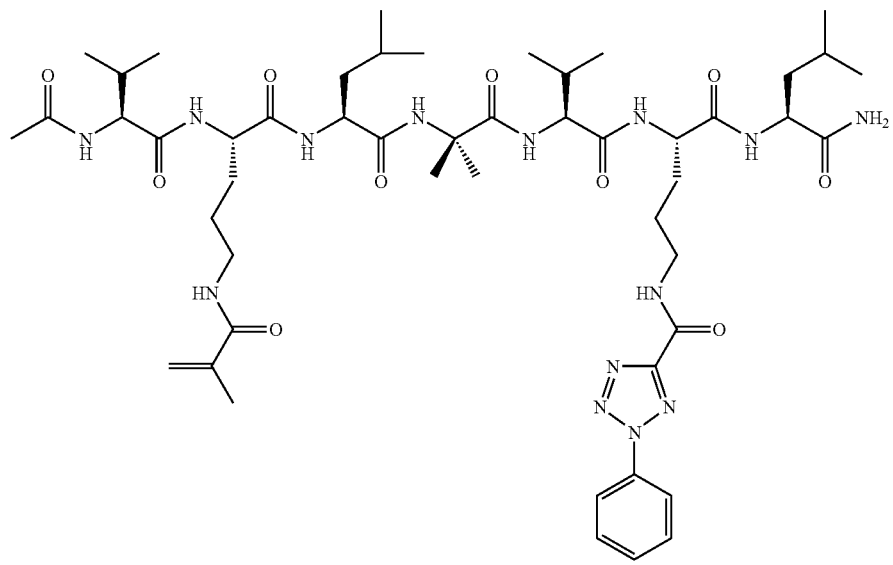

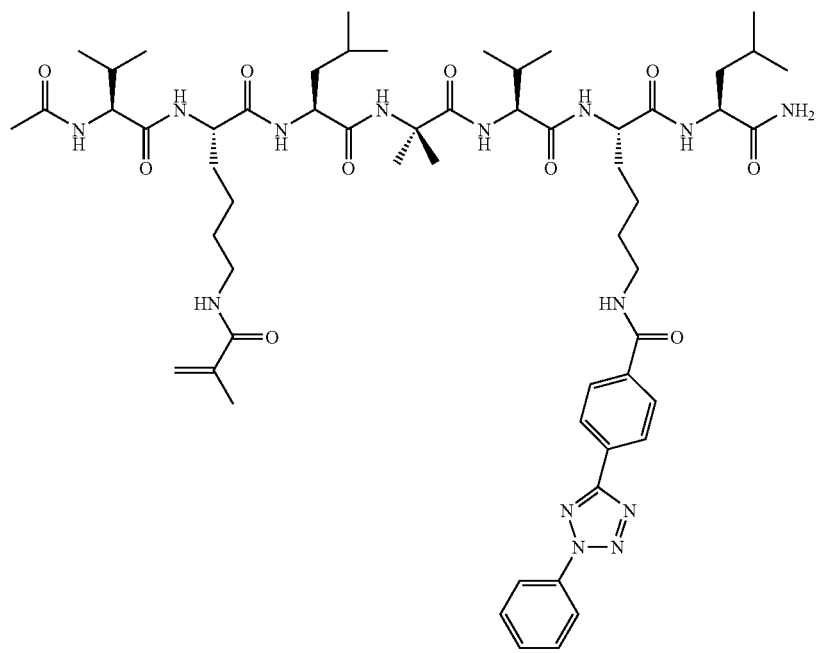

Linear peptide (4) (SEQ ID NO:1): Heptapeptide 4 was prepared according to the general procedure described above. After purification, a yellow-white crystalline solid was obtained in 11% yield (based on resin substitution): $^1$H-NMR (CD$_3$OD, 500 MHz) δ 8.34 (d, J=8.3 Hz, 2H), 8.25 (d, J=7.4 Hz, 2H), 8.04 (d, J=8.7 Hz 2H), 7.69 (t, J=8.1 Hz, 2H), 7.62 (t, J=7.2 Hz, 1H), 5.67 (s, 1H), 5.34 (s, 1H), 4.40 (dd, J=7.6, 3.7 Hz, 1H), 4.15 (m, 3H), 3.97 (d, J=6.7 Hz, 1H), 3.85 (d, J=7.0 Hz, 1H), 3.44 (br, m, 2H), 3.22 (br, m, 2H), 2.26 (br, m, 1H), 2.10 (s, 1H), 2.08-1.95 (br, m, 3H), 1.92 (s, 3H), 1.84-1.65 (br, m, 12H), 1.55 (m, 2H), 1.52 (s, 3H), 1.48 (s, 3H), 1.40-1.28 (br, m, 2H), 1.10-0.99 (br, m, 26H); HRMS (ESI) calcd for C$_{58}$H$_{88}$N$_{14}$O$_{10}$Na 1163.6700 [M+Na$^+$], found 1163.6722.

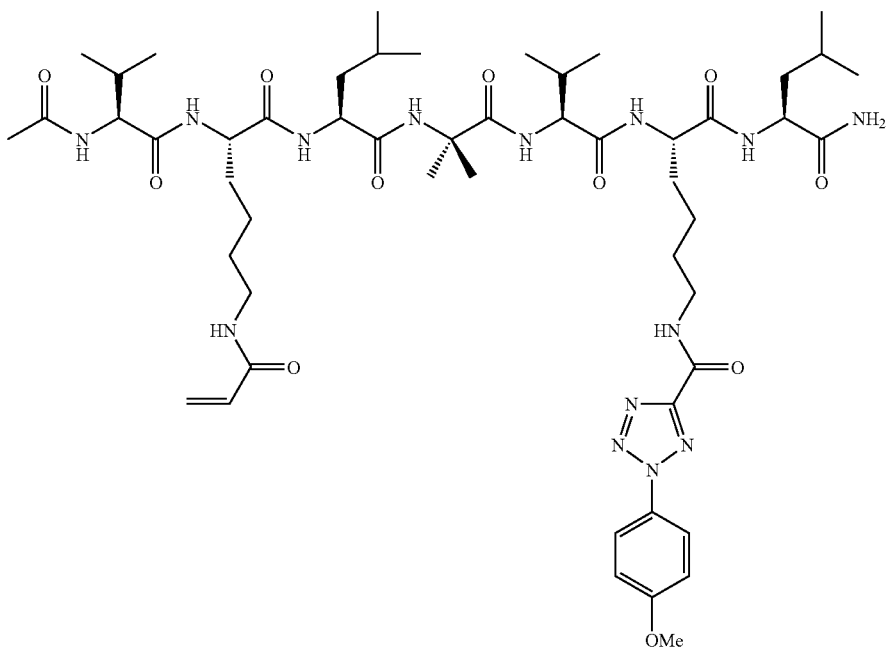

Linear Peptide (5) (SEQ ID NO:1): Heptapeptide 5 was prepared according to the general procedure. After RP-HPLC a yellowish white powder was obtained in 18% yield based on resin substitution: $^1$H-NMR (CD$_3$OD, 500 MHz) δ 8.09 (d, J=7.0 Hz, 2H), 7.17 (d, J=7.1 Hz, 2H), 6.20 (d, J=8.6 Hz, 2H), 5.62 (dd, J=8.6, 3.4 Hz, 1H), 4.37 (dd, J=11.3, 3.7 Hz 1H), 4.14 (m, 3H), 3.94 (d, J=6.7 Hz, 1H), 3.83 (s, 3H), 3.61 (m, 2H), 3.81 (d, J=7.1 Hz, 1H) 3.44 (m, 4H), 3.22 (m, 2H), 3.16 (m, 2H), 2.05 (s, 3H), 1.93 (m, 1H), 1.78-1.60 (br, m, 10H), 1.55-1.44 (br, m, 10H), 1.02-0.84 (br, m, 25H); HRMS (ESI) calcd for C$_{52}$H$_{84}$N$_{14}$P$_{11}$Na 1103.6342 [M+Na$^+$], found 1103.6351.

Linear Peptide (6) (SEQ ID NO:1): Heptapeptide 6 was prepared according to the general procedure. After RP-HPLC a yellowish white powder was obtained in 7% yield based on resin substitution: $^1$H-NMR (CD$_3$OD, 500 MHz) δ 8.10 (d, J=9.0 Hz, 2H), 7.18 (d, J=9.0 Hz, 2H), 5.65 (s, 1H), 5.32 (s, 1H), 4.37 (dd, J=11.3, 3.4 Hz, 1H), 4.13 (m, 3H), 3.94 (d, J=6.7 Hz, 1H), 3.90 (s, 3H), 3.81 (d, J=6.7 Hz, 1H), 3.44 (m, 4H), 3.22 (m, 2H), 3.16 (m, 2H), 2.05 (s, 3H), 1.93 (m, 1H), 1.78-1.60 (br, m, 10H), 1.55-1.44 (br, m, 13H), 1.02-0.84 (br,

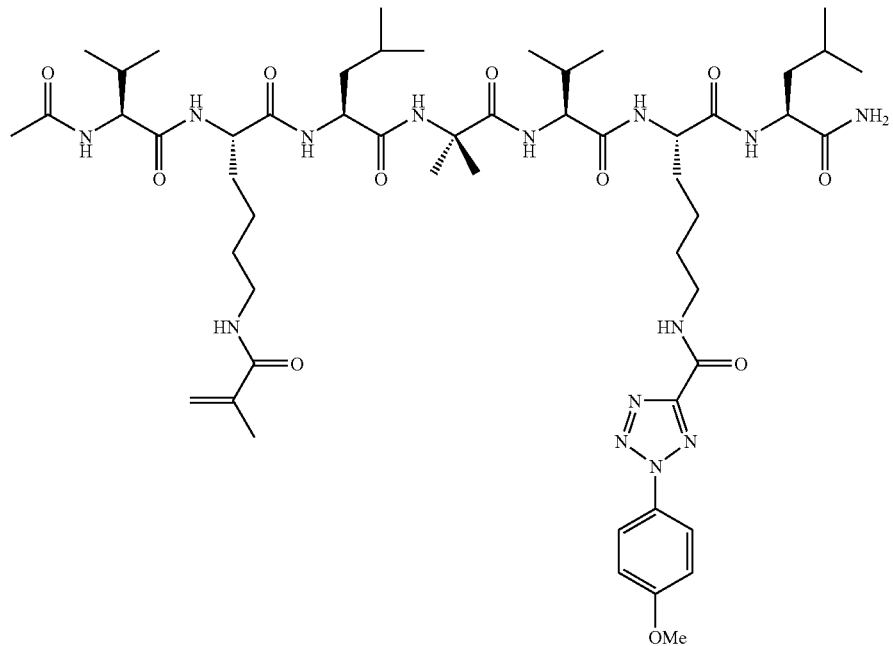

m, 25H); HRMS (ESI) calcd for C$_{53}$H$_{86}$N$_{14}$O$_{11}$Na 1117.6498 [M+Na$^+$], found 1117.6501.

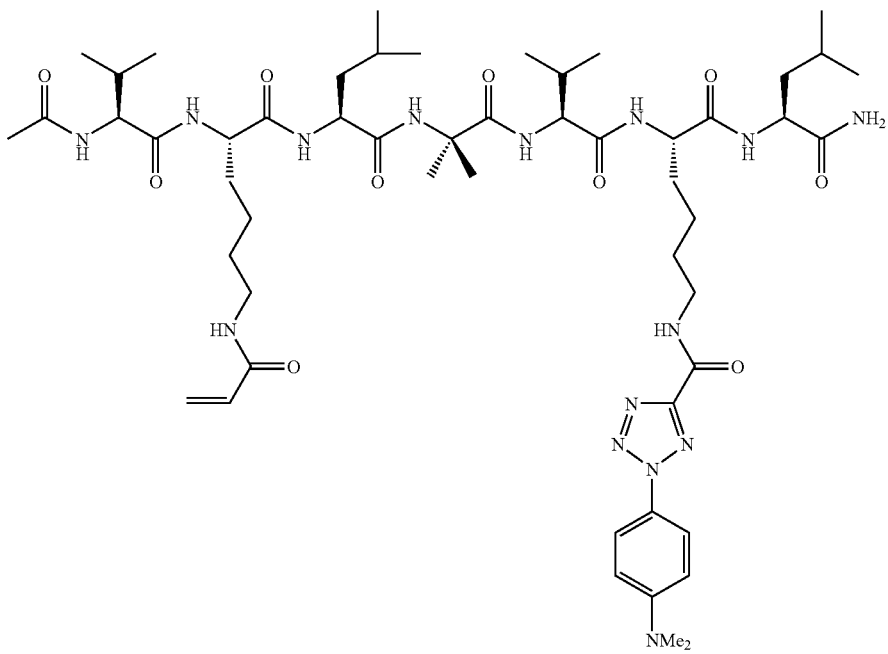

Linear Peptide (7) (SEQ ID NO:1): Heptapeptide 7 was prepared according to the general procedure. After RP-HPLC a yellowish white powder was obtained in 4% yield based on resin substitution: $^1$H-NMR (CD$_3$OD, 500 MHz) δ 7.97 (d, J=9.1 Hz, 2H), 6.93 (d, J=9.2 Hz, 2H), 6.23 (d, J=8.5 Hz, 2H), 5.65 (dd, J=8.7, 3.8 Hz, 1H), 4.41 (dd, J=10.9, 4.9 Hz, 1H), 4.14 (m, 3H), 3.97 (d, J=7.0 Hz, 1H), 3.47 (m, 4H), 3.25 (m, 4H), 3.09 (s, 6H) 2.05 (s, 3H), 1.93 (m, 1H), 1.78-1.60 (br, m, 10H), 1.55-1.44 (br, m, 10H), 1.02-0.84 (br, m, 25H); HRMS (ESI) calcd for C$_{53}$H$_{87}$N$_{15}$O$_{10}$Na 1116.6658 [M+Na$^+$], found 1116.6680.

Linear Peptide (8) (SEQ ID NO:1): Heptapeptide 8 was prepared according to the general procedure. After RP-HPLC a yellowish white powder was obtained in 2% yield based on resin substitution: $^1$H-NMR (CD$_3$OD, 400 MHz) δ 7.97 (d, J=9.2 Hz, 2H), 6.92 (d, J=9.1 Hz, 2H), 5.65 (s, 1H), 5.32 (s, 1H), 4.38 (dd, J=8.1, 2.9 Hz, 1H), 4.14 (m, 3H), 3.94 (d, J=6.6 Hz, 1H), 3.81 (d, J=8.9 Hz, 1H) 3.44 (m, 3H), 3.16 (m, 4H), 3.06 (s, 6H), 2.05 (s, 3H), 1.93 (m, 1H), 1.78-1.60 (br, m, 10H), 1.55-1.44 (br, m, 13H), 1.02-0.84 (br m, 25H). HRMS (ESI) calcd for C$_{54}$H$_{89}$N$_{15}$O$_{10}$Na 1130.6815 [M+Na$^+$], found 1130.6799.

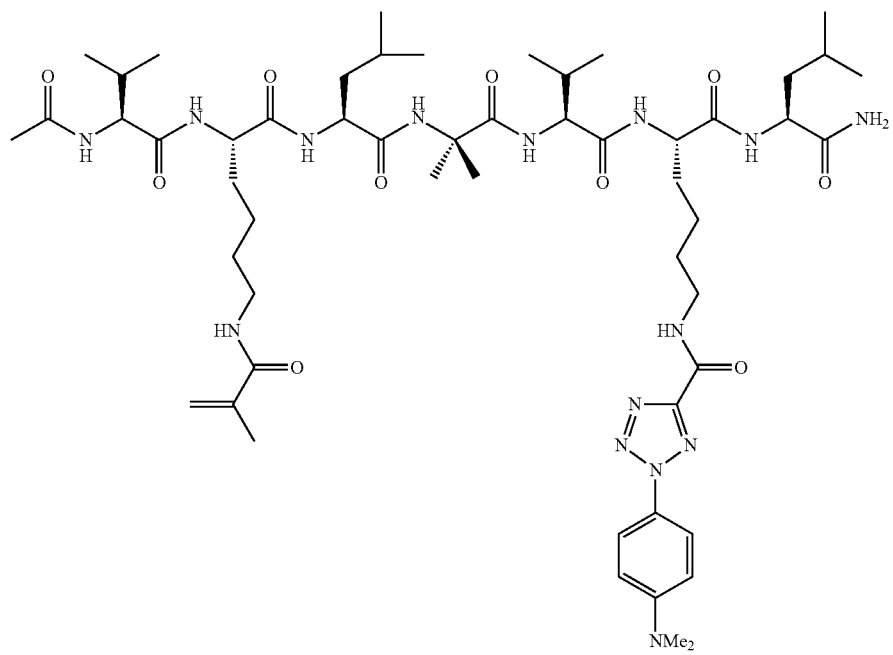

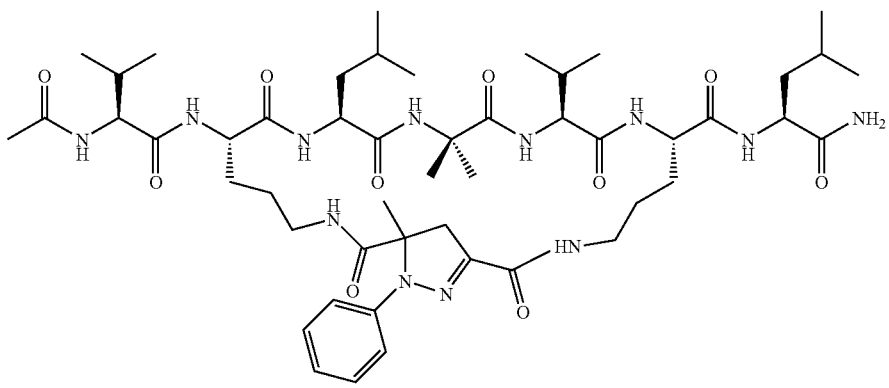

Cyclic Peptide (9) (SEQ ID NO:1): 15 milligrams of 1 was used in the photoactivated cycloaddition reaction to yield 2.2 mg cyclic peptide as a fluffy white powder (15%): $^1$H-NMR (CD$_3$OD, 500 MHz) δ 7.25 (t, J=7.5 Hz, 2H), 7.11 (d, J=7.8 Hz, 2H), 6.94 (t, J=7.4 Hz, 1H), 4.32 (br, m, 2H), 4.00 (t, J=7.3 Hz, 1H), 3.90 (m, 1H), 3.81 (d, J=6.5 Hz, 1H), 3.79-3.68 (br, m, 2H), 3.16-3.08 (br, m, 2H), 2.83 (m, 1H), 2.17 (m, 1H), 2.09 (s, 3H), 2.06 (s, 1H), 1.95-1.60 (br, m, 13H), 1.52 (d, J=6.4 Hz, 5H), 1.44 (s, 3H), 1.20 (m, 1H), 1.07-0.86 (br, m, 24H); HRMS (ESI) calcd for C$_{50}$H$_{80}$N$_{12}$O$_{10}$Na 1031.6013 [M+Na$^+$], found 1031.6028.

Cyclic Peptide (11) (SEQ ID NO:1): 20 milligrams of 3 was used in the photoactivated cycloaddition reaction to yield 8.2 mg cyclic peptide as a fluffy white powder (41%): $^1$H-NMR (CD$_3$OD, 500 MHz) δ 7.25 (t, J=7.3 Hz, 2H), 7.15 (m, 2H), 6.94 (t, J=7.3 Hz, 1H), 4.36 (m, 1H), 4.12 (m, 1H), 4.03 (t, J=7.0 Hz, 1H), 3.90 (dd, J=8.8, ?? Hz, 2H), 3.72 (m, 1H), 3.52 (m, 1H), 3.25 (m, 3H), 3.08 (m, 2H), 2.18 (m, 1H), 2.06 (s, 3H), 2.03 (s, 1H), 1.91 (br, m, 4H), 1.75-1.53 (br, m, 14H), 1.48 (s, 3H), 1.44 (d, J=1.7 Hz, 3H), 1.42 (s, 1H), 1.24 (m, 3H), 1.14 (t, J=7.1 Hz, 1H), 0.95-0.87 (br, m, 13H), 0.83-0.78 (br, m, 9H); HRMS (ESI) for C$_{52}$H$_{84}$N$_{12}$O$_{10}$Na 1059.6326 [M+Na$^+$], found 1059.6356.

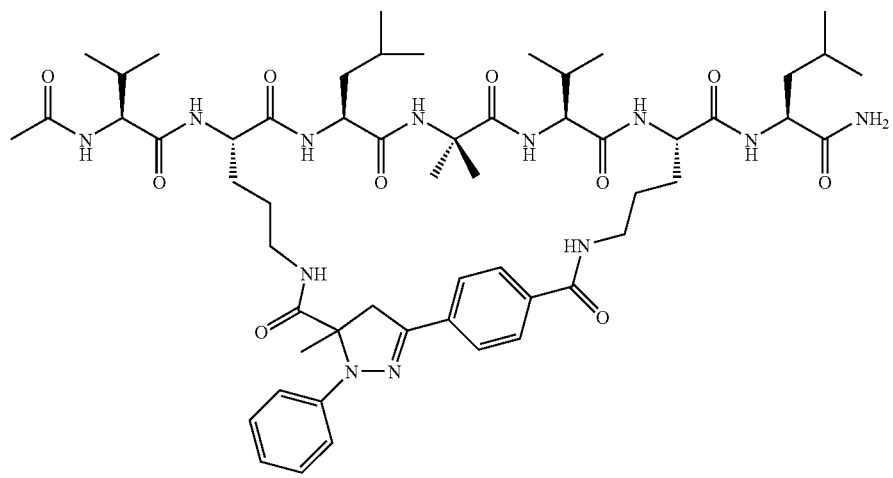

Cyclic Peptide (10) (SEQ ID NO:1): 18.5 milligrams of 2 was used in the photoactivated cycloaddition reaction to yield 2.8 mg cyclic peptide as a fluffy white powder (15%): $^1$H-NMR (CD$_3$OD, 500 MHz) δ 7.77 (d, J=8.7 Hz, 2H), 7.65 (d, J=8.6 Hz, 2H), 7.29 (t, J=8.1 Hz, 2H), 7.21 (d, J=7.7 Hz, 2H), 6.88 (t, J=7.3 Hz, 1H), 4.49 (m, 1H), 4.35 (m, 1H), 4.07 (m, 3H), 3.85 (m, 2H), 3.71 (br, m, 2H), 3.44 (q, 1H), 3.16 (q, 1H), 3.04 (br, m, 1H), 2.18 (s, 3H), 2.10 (br, m, 3H), 1.75 (br, m, 9H), 1.59 (s, 3H), 1.48 (s, 6H), 1.44 (s, 3H), 1.42 (s, 1H), 1.09-0.88 (br, m, 24H); HRMS (ESI) calcd for C$_{56}$H$_{84}$N$_{12}$O$_{10}$Na 1107.6326 [M+Na$^+$], found 1107.6368.

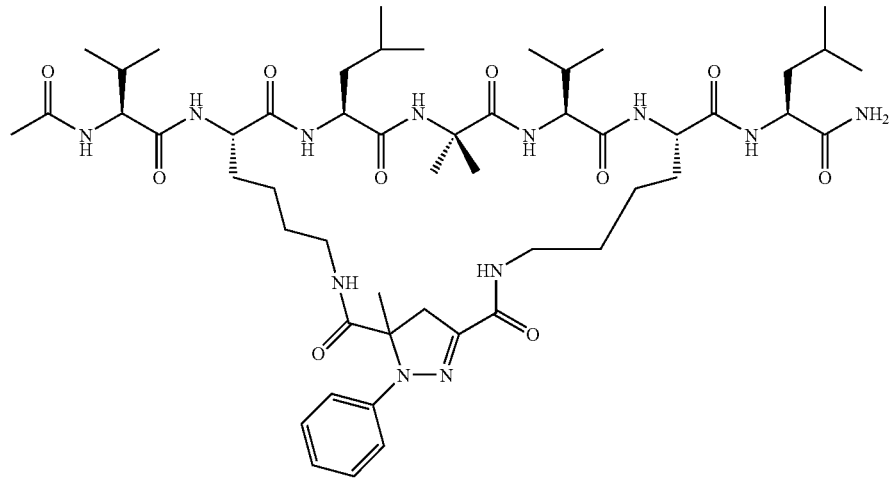

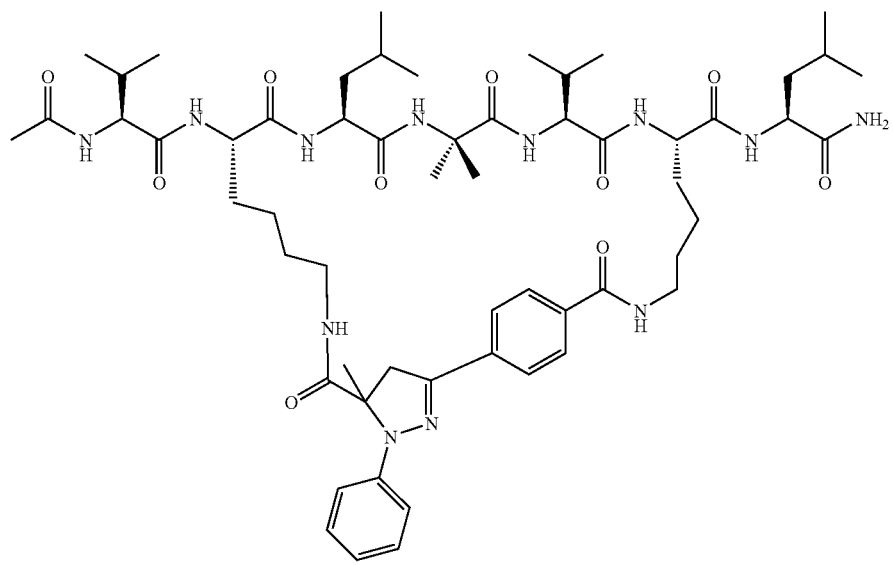

Cyclic Peptide (12) (SEQ ID NO:1): 20 milligrams of 4 was used in the photoinduced cycloaddition reaction to yield 7.5 mg cyclic peptide as a fluffy white powder (38%): $^1$H-NMR (CD$_3$OD, 500 MHz) δ 7.83 (d, J=8.5 Hz, 2H), 7.73 (d, J=8.5 Hz, 2H), 7.29 (t, J=8.5 Hz, 2H), 7.20 (d, J=7.5 Hz, 2H), 6.88 (t, J=7.5 Hz, 1H), 4.40 (m, 1H), 4.29 (t, J=8.5 Hz, 1H), 4.18 (m, 2H), 4.05 (d, J=10.5 Hz, 1H), 3.88 (d, J=5.0 Hz, 1H), 3.82 (d, J=5.5 Hz, 1H), 3.74 (d, J=12.5 Hz, 1H), 3.66 (m, 1H), 3.55 (m, 1H), 3.47 (m, 2H), 3.16 (m, 1H), 2.06 (s, 3H), 2.03 (s, 1H), 1.91 (br, m, 4H), 1.75-1.53 (br, m, 14H), 1.48 (s, 3H), 1.44 (d, J=1.7 Hz, 3H), 1.24 (m, 3H), 0.95-0.78 (br, m, 23H); HRMS (ESI) calcd for C$_{58}$H$_{88}$N$_{12}$O$_{10}$Na 1135.6639 [M+Na$^+$], found 1135.6650.

Cyclic Peptide (13) (SEQ ID NO:1): 15.0 mg of 5 was used in the photoinduced cycloaddition reaction to yield 9.1 mg cyclic peptide as a fluffy white powder in 64% yield: $^1$H-NMR (CD$_3$OD, 500 MHz) δ 7.05 (d, J=9.0 Hz, 2H), 6.87 (d, J=9.1 Hz, 2H), 4.68 (m, 1H), 4.36 (m, 2H), 4.17 (m, 1H), 4.13 (m, 2H), 3.98 (m, 1H), 3.89 (d, J=5.7 Hz, 1H), 3.74 (s, 3H) 3.61 (m, 2H), 3.44 (s, 1H), 2.18 (m, 1H), 2.05 (s, 3H), 1.72-1.56 (br, m, 12H), 1.48-1.28 (br, m, 12H), 1.05-0.87 (br, m, 25H); HRMS (ESI) calcd for C$_{52}$H$_{84}$N$_{12}$O$_{11}$Na 1075.6280 [M+Na$^+$], found 1075.6279.

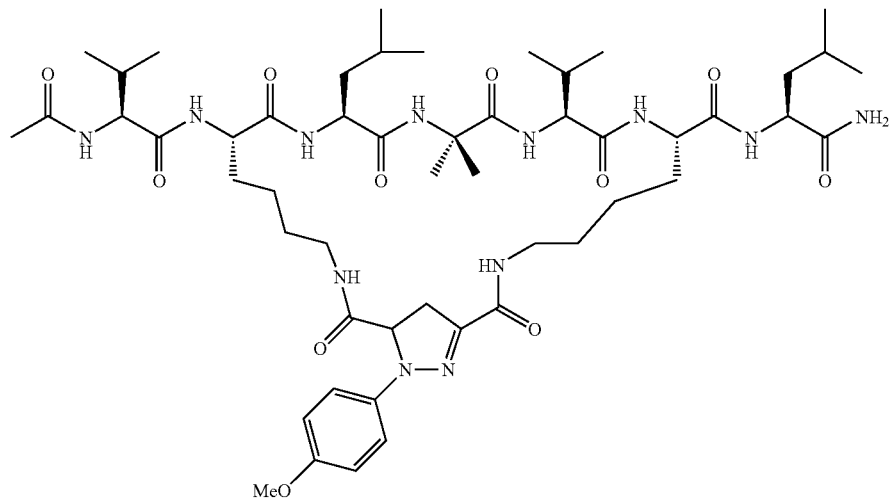

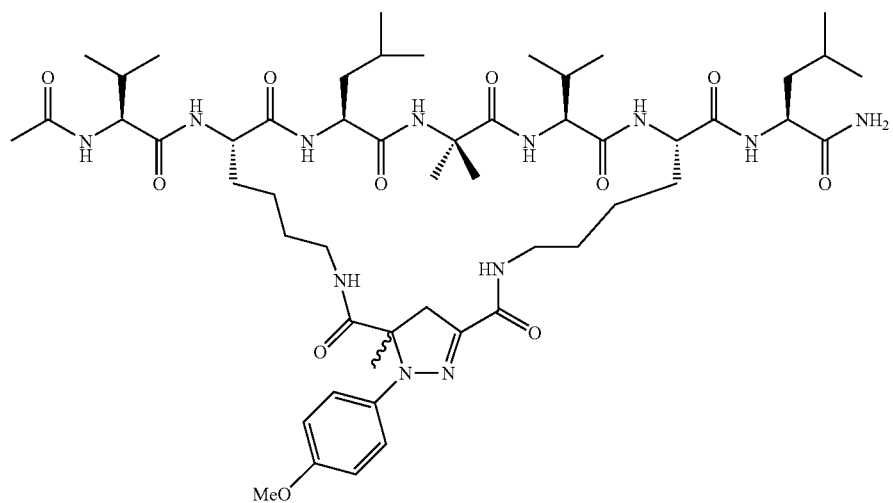

Cyclic Peptide (14) (SEQ ID NO:1): 10.1 milligrams of 6 was used in the photoinduced cycloaddition reaction to yield 5.3 mg cyclic peptide as a fluffy white powder in 53% yield: $^1$H-NMR (CD$_3$OD, 500 MHz) δ 7.09 (d, J=9.1 Hz, 2H), 6.85 (d, J=9.1 Hz, 2H), 6.20 (d, J=8.6 Hz, 2H), 5.62 (dd, J=8.6, 3.4 Hz, 1H), 4.37 (dd, J=11.3, 3.7 Hz, 1H), 4.14 (m, 3H), 3.94 (d, J=6.7 Hz, 1H), 3.83 (s, 3H), 3.61 (m, 2H), 3.81 (d, J=7.1 Hz, 1H), 3.44 (m, 4H), 3.16 (m, 2H), 2.05 (s, 3H), 1.93 (m, 1H), 1.78-1.60 (br, m, 10H), 1.55-1.44 (br, m, 10H), 1.02-0.84 (br, m, 25H); HRMS (ESI) calcd for C$_{53}$H$_{86}$N$_{12}$O$_{11}$Na 1089.6437 [M+Na$^+$], found 1089.6428.

Cyclic Peptide (15) (SEQ ID NO:1): 7.7 milligrams of 7 was used in the photo activated cyclo addition reaction to yield 4.4 mg cyclic peptide as a fluffy white powder in 64% yield. $^1$H-NMR (CD$_3$OD, 500 MHz) δ 7.02 (d, J=9.0 Hz, 2H), 6.83 (d, J=9.1 Hz, 2H), 4.89 (m, 1H), 4.38 (m, 2H), 4.19 (m, 1H), 4.12 (m, 2H), 3.98 (m, 1H), 3.90 (d, J=5.7 Hz, 1H), 3.59 (m, 2H), 3.44 (s, 1H), 3.07 (s, 6H) 2.18 (m, 1H), 2.05 (s, 3H), 1.72-1.56 (br m, 12H), 1.48-1.28 (br m, 12H), 1.05-0.87 (br m, 25H). HRMS (ESI) calcd for C$_{53}$H$_{87}$N$_{13}$O$_{10}$Na 1088.6597 [M+Na$^+$], found 1088.6585.

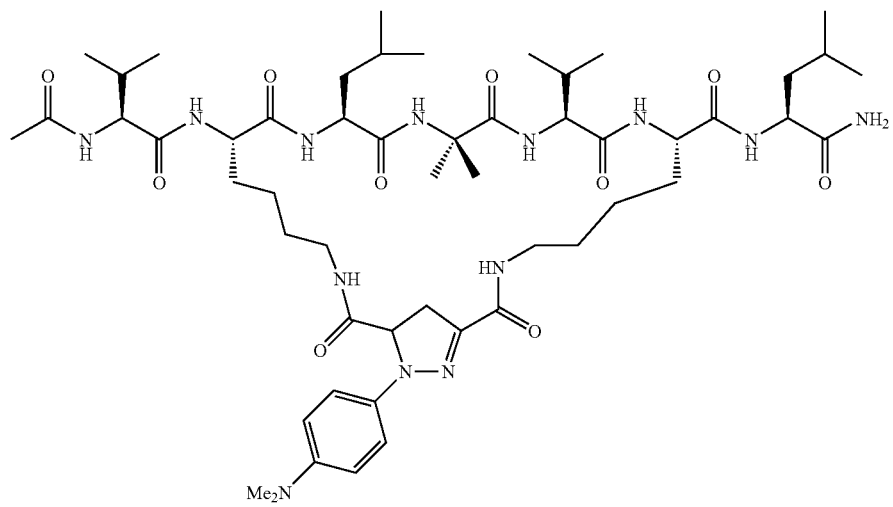

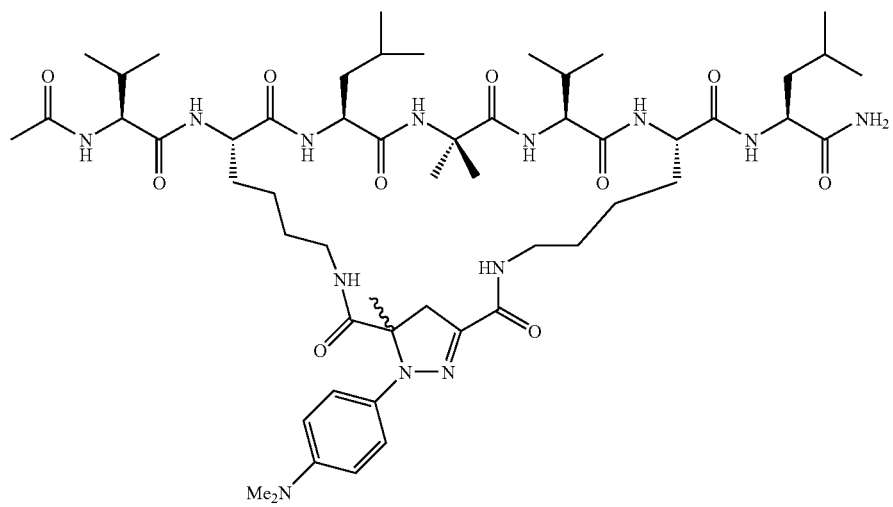

Cyclic Peptide (16) (SEQ ID NO:1): 3.4 milligrams of 8 was used in the photoinduced cyclo-addition reaction to yield 3.2 mg cyclic peptide as a fluffy white powder in 94% yield: $^1$H-NMR (CD$_3$OD, 500 MHz) δ 7.04 (d, J=9.1 Hz, 2H), 6.74 (d, J=9.1 Hz, 2H), 4.31 (dd, J=11.2, 3.5 Hz, 1H), 4.11 (m, 1H) 4.05 (dd, J=10.4, 3.6 Hz, 1H) 4.00 (t, J=7.1 Hz 1H), 3.91 (d, J=6.8 Hz, 1H), 3.86 (d, J=6.4 Hz, 1H), 4.32 (d, J=5.8 Hz, 1H) 3.67 (m, 1H), 3.39 (d, J=5.7 Hz, 1H), 3.18 (s, 2H), 3.84 (s, 6H), 2.18 (m, 1H), 2.05 (s, 3H), 1.72-1.56 (br, m, 12H), 1.48-1.28 (br, m, 12H), 1.05-0.87 (br, m, 25H); HRMS (ESI) calcd for C$_{54}$H$_{89}$N$_{13}$O$_{10}$Na 1102.6753 [M+Na$^+$], found 1102.6773.

Linear Peptide (17) (SEQ ID NO:1): Heptapeptide 17 was prepared according to the general procedure. After purification, a yellow-white crystalline solid was obtained in 5% yield (based on resin substitution): $^1$H-NMR (CD$_3$OD, 500 MHz) δ 8.25 (d, J=5.0 Hz, 1H), 8.20 (d, J=5.0 Hz, 1H), 7.97 (s, 1H), 7.78 (d, J=10.0 Hz, 1H), 7.69 (d, J=10.0 Hz, 1H), 7.62 (d, J=10.0 Hz, 1H), 7.55 (d, J=5.0 Hz, 1H), 4.35 (m, 1H), 4.09 (m, 3H), 3.92 (t, J=5.0 Hz, 1H), 3.81 (t, J=10.0 Hz, 1H), 3.17 (m, 4H), 2.21 (m, 1H), 2.08 (s, 4H), 1.92 (d, J=10.0 Hz, 8H), 1.82-1.60 (br, m, 9H), 1.49 (s, 7H), 1.44 (s, 7H), 1.06-0.86 (br, m, 24H); HRMS (ESI) calcd for C$_{44}$H$_{80}$N$_{10}$O$_{10}$Na 931.5951 [M+Na$^+$], found 931.5941.

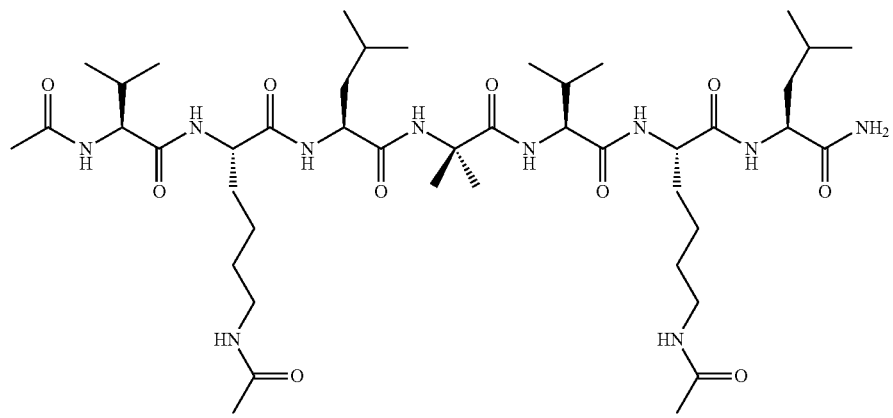

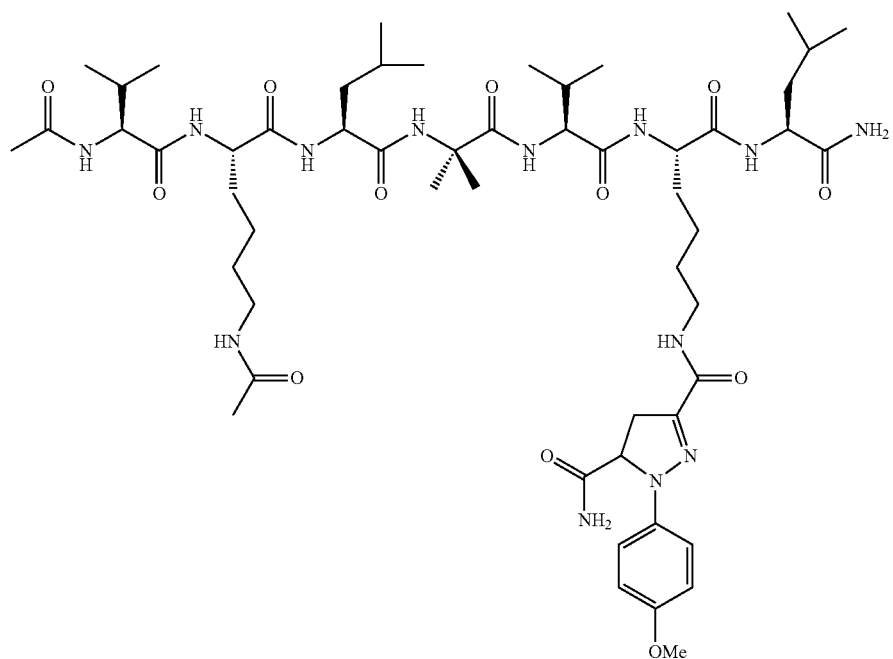

Linear Peptide (18) (SEQ ID NO:1): Heptapeptide 18 was prepared according to the general procedure. The tetrazole containing precursor was obtained as a yellow-white powder in 23% yield (25 mg, 23 μmole) based on resin substitution. The linear peptide was subjected to photoactivated 1,3-dipolar cycloaddition in the presence of 20 equiv of acrylamide (33 mg, 0.46 mmole) in 50 mL acetonitrile for 4 hours at 302 nm. Following the cycloaddition reaction, the mixture was concentrated and purified by reverse phase HPLC according to the general methods to give a yellow-white solid in 16% yield (4.0 mg): $^1$H-NMR (CD$_3$OD, 500 MHz) δ 7.81 (d, J=6.0 Hz, 1H), 7.72 (d, J=8.5 Hz. 1H), 7.55 (t, J=7.4, 2H), 7.42 (m, 1H), 7.40 (d, J=9.0 Hz, 2H), 7.28 (s, 1H), 7.06 (d, J=8.0 Hz, 1H), 7.01 (d, J=9.0 Hz, 2H), 6.98 (m, 2H), 4.36 (m, 3H), 4.19 (m, 2H), 4.12 (m, 5H), 3.95 (m, 1H), 3.84 (s, 3H), 3.81 (d, J=4.5 Hz, 1H), 3.65 (m, 1H), 3.44 (t, J=1.0 Hz, 1H), 3.16 (m, 3H), 2.18 (m, 1H), 2.05 (s, 3H), 1.72-1.56 (br, m, 12H), 1.48-1.28 (br, m, 12H), 1.05-0.87 (br, m, 25H); ESI-MS calcd for C$_{54}$H$_{90}$N$_{13}$O$_{12}$ 1112.7 [M+H$^+$], found 1112.5.

TABLE 1

Solvent tolerability study of the photoinduced stapling reaction[a]

| linear peptide | solvent | product | yield |
|---|---|---|---|
| 8 | MeCN | 16 | 87 |
| 8 | DCM | 16 | 43 |
| 8 | EtOAc | 16 | 86 |
| 8 | EtOH | 16 | 92 |
| 8 | $^i$PrOH | 16 | 88 |
| 8 | EtOH/H$_2$O (1:1) | 16 | 88 |

[a]The reaction was performed by irradiating 1.2 mL of 150 μM of peptide 8 in a quartz test tube with a handheld UV lamp at 302 nm for 10 minutes. The solvent was removed under the reduced pressure and the residue was subjected to the reverse-phase HPLC analysis equipped with a C$_{18}$ column. The yields were calculated based on the absorption at 254 nm in the HPLC traces.

Example 2

Cellular Uptake Study: HeLa cells cultured on cover slips were treated with 100 μM of peptide 13 or control peptide 18 in 2% DMSO serum-free DMEM medium for 4 hr in a 37° C., 5% CO$_2$ incubator. In preparation for fixation, medium was aspirated and the cells were washed twice with PBS. The cover slips were treated to a freshly prepared 4% paraformaldehyde/PBS solution for 10~15 min, washed twice with PBS, and quenched with 50 mM NH$_4$Cl for 10 minutes. After washing with PBS twice, the cover-slip was flipped and placed on top of microscopy glass containing in situ-frame and PBS buffer to make a sealed sample chamber. The images were acquired on a Zeiss Axioimager motorized fluorescence microscope. DAPI filter (ex 365 nm, em 445±25 nm) was used in acquiring fluorescence images. All image acquisitions and processing were performed under identical conditions.

Example 3

Example of Peptide Synthesis and In Vitro Inhibition Study

GST-MDM2 and GST-MDMX containing full-length human MDM2 and MDMX and His6-tagged human p53 were expressed in *Escherichia coli* and affinity purified by binding to glutathione-agarose and Ni$^{2+}$-nitrilotriacetic acid beads under non-denaturing conditions. ELISA plates were incubated with 2.5 μg/ml His6-p53 in phosphate-buffered saline (PBS) for 16 h. After washing with PBS+0.1% Tween 20 (PBST), the plates were blocked with PBS+5% nonfat dry milk+0.1% Tween 20 (PBSMT) for 0.5 hour. The peptides were dissolved in DMSO. GST-HDM2 and MDMX (5 μg/ml) were mixed with peptides in PBSMT+10% glycerol+10 mM dithiothreitol and added to the wells. The plates were washed with PBST after incubating for 1 hour at room temperature, incubated with MDM2 antibody 5B10 and MDMX antibody 8C6 in PBSMT for 1 hour, followed by washing and incubation with horseradish peroxidase-rabbit-anti-mouse Ig antibody for 1 hour. The plates were developed by incubation with TMB peroxidase substrate (KPL) and measured by absorbance at 450 nm.

TABLE 2

Inhibitory activities of the stapled peptides against Mdm2 and Mdmx as determined by ELISA assays.

SEQ ID NO: 1 Val Xaa Leu Gly Val Xaa Leu

| Peptide name | Sequence | charge | $IC_{50}$, Mdm2 (nM) | $IC_{50}$, Mdmx (nM) |
|---|---|---|---|---|
| P53 | ETFSDLWKLLPE (SEQ ID NO: 2) | 0 | 2,000 | 6,000 |
| PDI | LTFEHYWAQLTS (SEQ ID NO: 3) | −1 | 44 | 550 |
| sPDI-1 | ⌐L1⌐ LTFαHYWAQLβS (SEQ ID NO: 4) | 0 | 140 ± 1.5 | 750 ± 60 |
| sPDI-2 | ⌐L2⌐ LTFαHYWAQLβS (SEQ ID NO: 4) | 0 | 410 ± 60 | 1,300 ± 100 |
| sPDI-3 | ⌐L3⌐ LTFαHYWAQLβS (SEQ ID NO: 4) | 0 | 160 | 500 |
| sPDI-4 | ⌐L3⌐ LTFαHYWβQLTS (SEQ ID NO: 5) | 0 | 87 | 390 |
| sPDI-5 | ⌐L3⌐ LTFEαYWAβLTS (SEQ ID NO: 6) | −1 | 260 | 1,410 |
| sPDI-6 | ⌐L4⌐ LTFαHYWβQLTS (SEQ ID NO: 5) | 0 | 570 ± 170 | 3,900 ± 110 |
| sPDI-7 | ⌐L5⌐ LTFαHYWβQLTS (SEQ ID NO: 5) | 0 | 5,200 ± 300 | 27,000 ± 2,000 |
| sPDI-8 | ⌐L3⌐ LTFαHYWβRLTS (SEQ ID NO: 7) | +1 | 55 | 231 |
| sPDI-9 | ⌐L3⌐ LTFαHYWβRLRS (SEQ ID NO: 8) | +2 | 179 | 525 |
| sPMI-1 | ⌐L3⌐ TSFαQYWβLLSP (SEQ ID NO: 9) | 0 | 290 ± 24 | 330 ± 71 |
| sPMI-2 | ⌐L3⌐ TSFAαYWNβLSP (SEQ ID NO: 10) | 0 | 1,079 | 3,648 |
| sPMI-3 | ⌐L3⌐ TSFαQYWNLLβP (SEQ ID NO: 11) | 0 | 23 | 1,489 |
| sPMI-4 | ⌐L3⌐ TSFαRYWβRLSP (SEQ ID NO: 12) | +2 | 1,232 | 1,842 |
| sPMI-5 | ⌐L3⌐ TSFαQYWβRLRP (SEQ ID NO: 13) | +2 | 597 | 298 |

TABLE 3

ESI-MS characterization of the stapled peptides.

| Compound | Calculated mass ($M^+$, m/z) | Found mass (m/z) |
|---|---|---|
| PDI-1 | 1871.9 | 948.0 $[M + H + Na]^{2+}$ |
| sPDI-1 | 1843.9 | 1867.1 $[M + Na]^+$ |
| sPDI-2 | 1841.9 | 971.7 $[M + NMP + 2H]^{2+}$ |
| sPDI-3 | 1831.7 | 1832.8 $[M + H]^+$ |
| sPDI-4 | 1834.7 | 1835.9 $[M + H]^+$ |
| sPDI-5 | 1792.7 | 1792.8 $[M + H]^+$ |
| sPDI-6 | 1890.7 | 1892.0 $[M + H]^+$ |
| sPDI-7 | 1932.7 | 967.3 $[M + 2H]^{2+}$ |
| sPDI-8 | 1862.8 | 1863.9 $[M + 1H]1+$ |
| sPDI-9 | 1917.8 | 959.9 $[M + 2H]^{2+}$ |
| sPMI-1 | 1723.7 | 1746.8 $[M + Na]^+$ |
| sPMI-2 | 1780.7 | 1803.9 $[M + Na]^+$ |
| sPMI-3 | 1806.8 | 1829.9 $[M + Na]^+$ |
| sPMI-4 | 1850.9 | 1852.1 $[M + H]^+$ |
| sPMI-5 | 1892.9 | 1894.0 $[M + H]^+$ |

All peptides in Tables 2 and 3 were amidated at the C-termini and acetylated at the N-termini. The cross-linker structures are shown as follows:

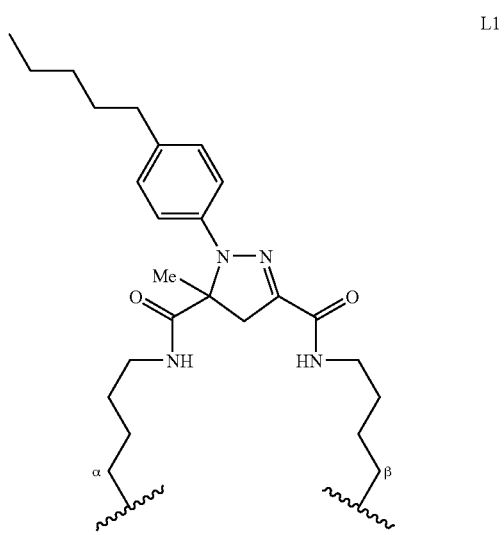

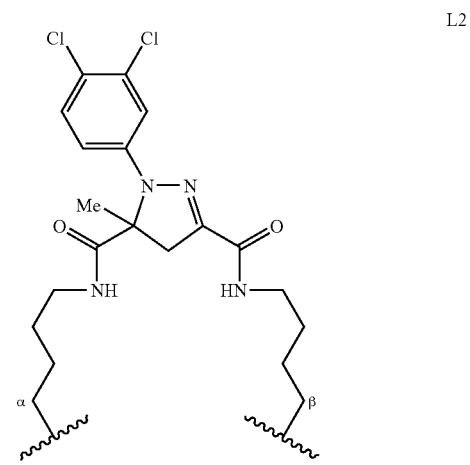

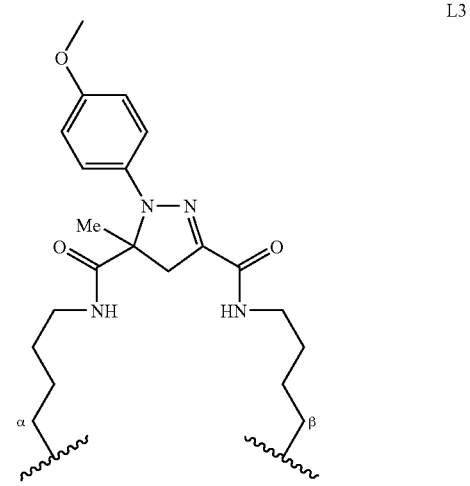

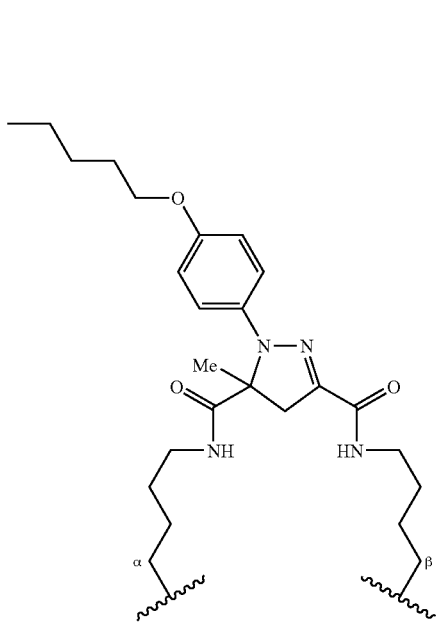

L4

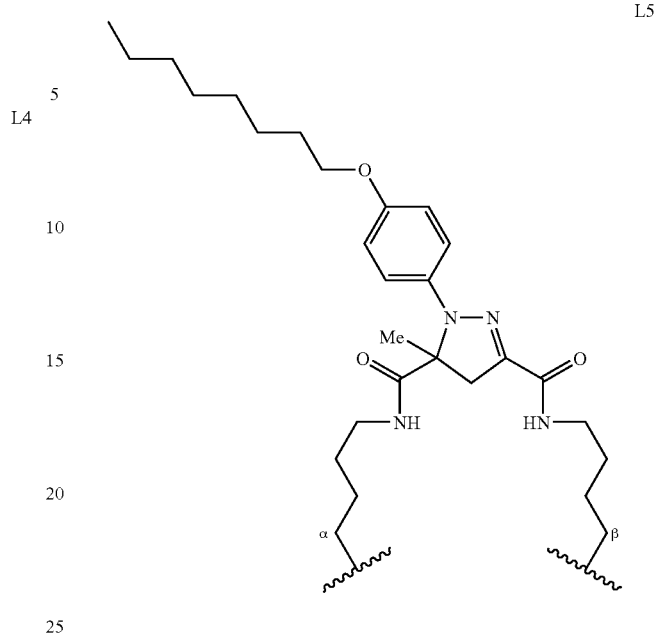

L5

While the invention has been described through illustrative examples and embodiments, routine modifications to the described examples and embodiments will be apparent to those skilled in the art and such modifications are intended to be within the scope of the present invention.

The invention claimed is:

1. A method for preparation of a stapled peptide, comprising the steps of:
   a) providing a functionalized peptide, wherein the functionalized peptide comprises at least a first functionalized amino acid and a second functionalized amino acid, wherein the first functionalized amino acid comprises an alkene moiety and the second functionalized amino acid comprises a tetrazole moiety, wherein the second functionalized amino acid is the fourth or the seventh successive amino acid from the first functionalized amino acid, wherein the alkene and tetrazole moieties can react to form a pyrazoline moiety and the stapled peptide can exhibit helical secondary structure; and
   b) exposing the functionalized peptide to electromagnetic radiation of a wavelength from 300 to 320 nm such that a stapled peptide having a pyrazoline moiety, formed from reaction of the alkene moiety with the tetrazole moiety, and exhibiting helical secondary structure is formed.

2. The method of claim 1, wherein the functionalized peptide has a structure according to Formula I:

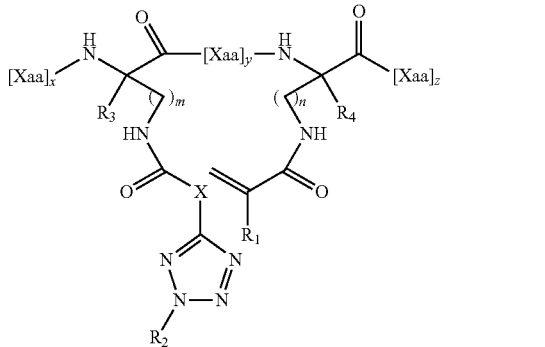

Formula I wherein,
$R_1$ is H or an alkyl group comprising 1 to 6 carbons,
$R_2$ is a phenyl group, a substituted phenyl group or a heterocyclic group,
$R_3$ is H or an alkyl group comprising 1 to 6 carbons,
$R_4$ is H or an alkyl group comprising 1 to 6 carbons,
X is a phenyl group, a substituted phenyl group, a heterocyclic group, or a direct linkage,
m is an integer from 1 to 6,
n is an integer from 1 to 6,
[Xaa] is any natural or synthetic amino acid,
x is an integer from 1 to 10,
y is 3 or 6, and
z is an integer from 1 to 10,
wherein the stapled peptide has a structure according to Formula II:

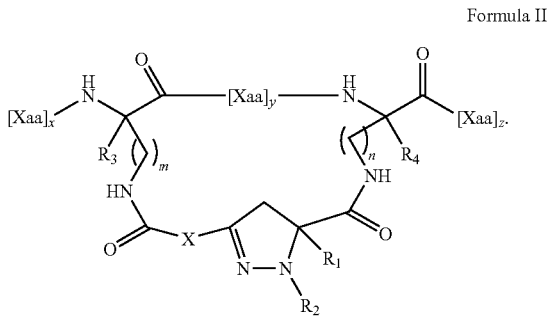

Formula II

3. The method of claim 2, wherein,
$R_1$ is H or methyl,
$R_2$ is a phenyl group or a substituted phenyl group selected from the group consisting of 4-methoxyphenyl group and N,N-dimethyl-4-aminophenyl group,
$R_3$ and $R_4$ are H,
X is a phenyl group or a direct linkage,
m and n are 3,
x and z are 1, and
y is 3.

4. The method of claim 1, wherein the functionalized peptide is capable of forming an alpha-helix.

5. The method of claim 1, wherein the alkene group is a methacrylate group and $R_1$ is H or a methyl group.

* * * * *